United States Patent [19]

Van Duzer et al.

[11] Patent Number: 5,350,761

[45] Date of Patent: Sep. 27, 1994

[54] INDOLYL SUBSTITUTED HYDROXYLAMINE DERIVATIVES

[75] Inventors: John H. Van Duzer, Asbury; Dennis M. Roland, Basking Ridge, both of N.J.

[73] Assignee: Ciba-Geigy Corporation, Ardsley, N.Y.

[21] Appl. No.: 99,873

[22] Filed: Jul. 30, 1993

Related U.S. Application Data

[60] Division of Ser. No. 893,142, Jun. 3, 1992, Pat. No. 5,260,316, which is a continuation-in-part of Ser. No. 738,075, Jul. 30, 1991, abandoned.

[51] Int. Cl.$^5$ .................. A61K 31/405; C07D 209/12; C07D 209/34
[52] U.S. Cl. .................... 514/373; 514/414; 514/418; 548/207; 548/465; 548/467; 548/472
[58] Field of Search ............... 514/373, 414, 418; 548/207, 465, 467, 472

[56] References Cited

U.S. PATENT DOCUMENTS

| | | | |
|---|---|---|---|
| 4,738,986 | 4/1988 | Kneen et al. | 514/575 |
| 4,757,078 | 7/1988 | Misra | 546/141 |
| 4,769,461 | 9/1988 | Musser et al. | 546/152 |
| 4,792,560 | 12/1988 | Huang | 514/311 |
| 4,873,259 | 10/1989 | Summers, Jr. et al. | 514/443 |
| 4,981,865 | 1/1991 | Belliotti et al. | 514/480 |
| 5,004,747 | 4/1991 | Ashton et al. | 514/309 |
| 5,006,534 | 4/1991 | Mohrs et al. | 514/311 |
| 5,036,157 | 7/1991 | Kneen et al. | 562/623 |
| 5,084,575 | 1/1992 | Kreft, III et al. | 546/172 |
| 5,162,340 | 11/1992 | Chakravarty et al. | 514/309 |
| 5,210,196 | 11/1993 | von Oppolzer | 548/207 |

FOREIGN PATENT DOCUMENTS

| | | |
|---|---|---|
| 196184 | 10/1986 | European Pat. Off. |
| 0196184 | 10/1986 | European Pat. Off. |
| 0240859 | 10/1987 | European Pat. Off. |
| 0279263 | 8/1988 | European Pat. Off. |
| 292699 | 11/1988 | European Pat. Off. |
| 408760 | 1/1991 | European Pat. Off. |
| 0185070 | 8/1987 | Japan ........................ 548/472 |
| 0079874 | 4/1988 | Japan ........................ 548/472 |
| 9001929 | 3/1990 | PCT Int'l Appl. |
| 9008545 | 8/1990 | PCT Int'l Appl. |
| 9116298 | 10/1991 | PCT Int'l Appl. |
| 9203130 | 3/1992 | PCT Int'l Appl. |

OTHER PUBLICATIONS

Molecular Pharmacology, vol. 40, p. 22 (1991).

*Primary Examiner*—Mukund J. Shah
*Assistant Examiner*—Y. N. Gupta
*Attorney, Agent, or Firm*—Norbert Gruenfeld

[57] ABSTRACT

Disclosed are the compound of the formula

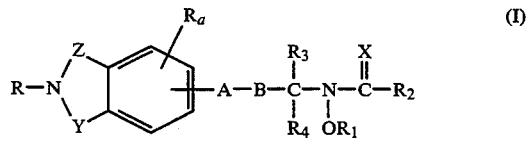

(I)

wherein

R represents hydrogen, lower alkyl, aryl, biaryl, $C_3$–$C_7$-cycloalkyl, aryl-lower alkyl, aryl-lower alkenyl, aryl-lower alkynyl, aryloxy-lower alkyl, arylthio-lower alkyl, $C_3$–$C_7$-cycloalkyl-lower alkyl, biaryl-lower alkyl, aryl-$C_3$–$C_7$-cycloalkyl, aryl-$C_3$–$C_7$-cycloalkyl-lower alkyl or aryloxy-aryl-lower alkyl; and aryl represents carbocyclic or heterocyclic aryl;

Z represents $C_1$–$C_3$-alkylene or vinylene, each unsubstituted or substituted by lower alkyl;

Y represents $SO_2$ (sulfonyl) or CO (carbonyl);

A represents O (oxygen), S (sulfur), or a direct bond;

B represents lower alkylene; or B represents lower alkenylene provided that A represents a direct bond;

X represents oxygen or sulfur, $R_1$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$–$C_7$-cycloalk- (Abstract continued on next page.)

ylaminocarbonyl or $C_3$–$C_7$-cycloalkyl-lower alkylaminocarbonyl;

$R_2$ represents lower alkyl, lower alkoxycarbonyl-lower alkyl, $C_3$–$C_7$-cycloalkyl, carbocyclic or heterocyclic aryl, carbocyclic or heterocyclic aryl-lower alkyl, $C_3$–$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$–$C_7$-cycloalkylamino, $C_3$–$C_7$-cycloalkyl-lower alkylamino or lower alkoxycarbonyl-lower alkylamino;

$R_3$ and $R_4$ independently represent hydrogen or lower alkyl;

$R_a$ represents hydrogen, lower alkyl, halo, trifluoromethyl or lower alkoxy; and pharmaceutically acceptable salts thereof; which are useful as lipoxygenase inhibitors.

7 Claims, No Drawings

INDOLYL SUBSTITUTED HYDROXYLAMINE DERIVATIVES

CROSS REFERENCE TO RELATED APPLICATIONS

This is a divisional of Ser. No. 07/893,142, filed Jun. 3, 1992, which is now U.S. Pat. No. 5,260,316, which is a continuation-in-part of Ser. No. 07/738,075, filed Jul. 30, 1991, now abandoned.

SUMMARY OF THE INVENTION

The invention relates to the substituted hydroxylamine derivatives as defined herein which are particularly useful as selective lipoxygenase inhibitors, methods for preparation thereof, pharmaceutical compositions comprising said compounds, and a method of inhibiting lipoxygenase, in particular 5-lipoxygenase, and of treating diseases in mammals which are responsive to lipoxygenase inhibition, using said compounds or pharmaceutical compositions comprising said compounds of the invention.

The compounds of the invention are particularly useful for the prevention and treatment of various inflammatory and allergic conditions, e.g. bronchial allergies and inflammatory disorders such as asthma, allergic rhinitis (hay fever), ocular allergies and inflammation, inflammatory bowel disease (including Crohn's disease, ulcerative colitis), and dermatological allergies and inflammation such as eczema and psoriasis; also for the treatment of rheumatic disorders such as rheumatoid arthritis, osteoarthritis and gouty arthritis; also for the treatment of ischemic conditions such as myocardial infarction and cerebral ischemia; also for the treatment of multiple sclerosis; for the treatment of endotoxin shock; for the treatment of renal disorders, such as primary nephrotic syndrome and cyclosporine-induced renal toxicity; in the treatment of certain carcinomas, e.g. to inhibit tumor metastasis; also to inhibit gastrointestinal side effects of non-steroidal antiinflammatory drugs.

DETAILED DESCRIPTION OF THE INVENTION

More particularly the invention relates to the compounds of formula I

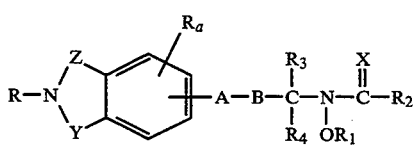

wherein

R represents hydrogen, lower alkyl, aryl, biaryl, $C_3-C_7$-cycloalkyl, aryl-lower alkyl, aryl-lower alkenyl, aryl-lower alkynyl, aryloxy-lower alkyl, arylthio-lower alkyl, $C_3-C_7$-cycloalkyl-lower alkyl, biaryl-lower alkyl, aryl-$C_3-C_7$-cycloalkyl, aryl-$C_3-C_7$-cycloalkyl-lower alkyl or aryloxy-aryl-lower alkyl; and aryl represents carbocyclic or heterocyclic aryl;

Z represents $C_1-C_3$-alkylene or vinylene, each unsubstituted or substituted by lower alkyl;

Y represents $SO_2$(sulfonyl) or CO (carbonyl);

A represents O (oxygen), S (sulfur), or a direct bond;

B represents lower alkylene; or B represents lower alkenylene provided that A represents a direct bond;

X represents oxygen or sulfur, $R_1$ represents hydrogen, acyl, lower alkoxycarbonyl, aminocarbonyl, mono-or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3-C_7$-cycloalkylaminocarbonyl or $C_3-C_7$-cycloalkyl-lower alkylaminocarbonyl;

$R_2$ represents lower alkyl, lower alkoxycarbonyl-lower alkyl, $C_3-C_7$-cycloalkyl, carbocyclic or heterocyclic aryl, carbocyclic or heterocyclic aryl-lower alkyl, $C_3-C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3-C_7$-cycloalkylamino, $C_3-C_7$-cycloalkyl-lower alkylamino or lower alkoxycarbonyl-lower alkylamino;

$R_3$ and $R_4$ independently represent hydrogen or lower alkyl;

$R_a$ represents hydrogen, lower alkyl, halo, trifluoromethyl or lower alkoxy; and pharmaceutically acceptable salts thereof.

The point of attachment at grouping A of the chain to the ring may be at any of the available positions of the benzene ring, preferably meta or para to Y or Z.

Embodiments of the invention relate to compounds wherein, in formula I, Y represents CO and those wherein, in formula I, Y represents $SO_2$.

Particular embodiments of the invention relate to the ring systems involved, i.e. compounds wherein, in formula I, Y represents CO and Z represents ethylene or vinylene; compounds of formula I wherein Y represents $SO_2$ and Z represents ethylene or vinylene; compounds wherein, in formula I, Z represents methylene and Y represents CO; compounds wherein, in formula I, Z represents methylene and Y represents $SO_2$; compounds wherein, in formula I, Z represents 1,3-propylene and Y represents CO; compounds wherein, in formula I, Z represents 1,3-propylene and Y represents $SO_2$.

Further embodiments of the invention relate to the said compounds wherein X represents oxygen in formula I, and those wherein X represents sulfur in formula I.

Preferred are said compounds wherein, in formula I, $R_1$ represents hydrogen and $R_2$ represents optionally substituted amino, i.e. amino, mono- or di-lower alkylamino, lower alkenylamino, lower alkynylamino, carbocyclic or heterocyclic aryl-lower alkylamino, carbocyclic or heterocyclic arylamino, $C_3-C_7$-cycloalkylamino, $C_3-C_7$-cycloalkyl-lower alkylamino or lower alkoxycarbonyl-lower alkylamino; and other symbols have meaning as defined above.

Also preferred are said compounds wherein R represents biaryl-lower alkyl.

A preferred embodiment of the invention relates to compounds of formula II

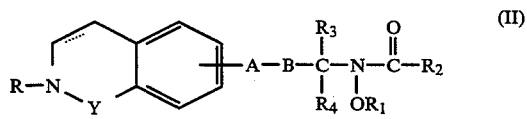

wherein R represents hydrogen, lower alkyl, carbocyclic or heterocyclic aryl-lower alkyl, carbocyclic aryl-lower alkenyl, carbocyclic or heterocyclic aryloxy-lower alkyl, carbocyclic or heterocyclic arylthio-lower alkyl. $C_3$-$C_7$-cycloalkyl-lower alkyl, biaryl-lower alkyl or carbocyclic aryloxyaryl-lower alkyl; Y represents CO or $SO_2$; A represents oxygen, sulfur or a direct bond; B represents lower alkylene; or B represents lower alkenylene provided that A represents a direct bond; $R_1$ represents hydrogen or acyl; $R_2$ represents amino, mono- or di-lower alkylamino, lower alkenylamino, lower alkynylamino, carbocyclic or heterocyclic aryl-lower alkylamino, carbocyclic or heterocyclic arylamino, $C_3$-$C_7$-cycloalkylamino, $C_3$-$C_7$-cycloalkyl-lower alkylamino or lower alkoxycarbonyl-lower alkylamino; $R_3$ and $R_4$ independently represent hydrogen or lower alkyl; and pharmaceutically acceptable salts thereof.

The dotted line in the ring system of formula II or IV indicates that the bond involved is either a single or double bond.

Preferred are said compounds of formula II wherein Y represents CO or $SO_2$; A represents oxygen or a direct bond; B represents alkylene of 1 to 4 carbon atoms; R represents carbocyclic or heterocyclic aryloxy-lower alkyl, quinolyl-lower alkyl or biaryl-lower alkyl; $R_1$ and $R_4$ represent hydrogen; $R_2$ represents amino, mono- or di-lower alkylamino, lower alkenylamino, lower alkynylamino, carbocyclic aryl-lower alkylamino, carbocyclic arylamino or $C_3$-$C_7$-cycloalkylamino; $R_3$ represents hydrogen or lower alkyl; and pharmaceutically acceptable salts thereof.

Also preferred are compounds wherein, in formula II. Y represents CO or $SO_2$; A represents a direct bond; B represents alkenylene of 2 to 4 carbon atoms; R represents carbocyclic or heterocyclic aryl-lower alkyl, biaryl-lower alkyl or cyclohexyl-lower alkyl; $R_1$ and $R_4$ represent hydrogen; $R_2$ represents amino, mono- or di-lower alkylamino, lower alkenylamino, lower alkynylamino, carbocyclic aryl-lower alkylamino, carbocyclic arylamino or $C_3$-$C_7$-cycloalkylamino; $R_3$ represents hydrogen or lower alkyl; and pharmaceutically acceptable salts thereof.

Preferred in turn are the compounds of formula III

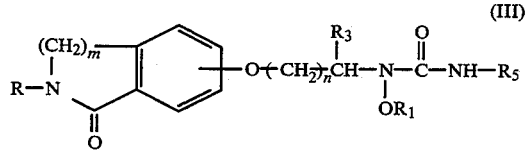

(III)

wherein R represents lower alkyl, biaryl-lower alkyl, carbocyclic or heterocyclic aryl-$C_1$-$C_4$-alkyl, carbocyclic or heterocyclic aryloxy-$C_1$-$C_4$-alkyl, carboxylic aryloxyaryl-$C_1$-$C_4$-alkyl, carbocyclic aryl-$C_3$ or $C_4$-alkenyl, or cyclohexyl-$C_1$-$C_4$-alkyl; m and n independently represent 1,2 or 3; $R_1$ represents hydrogen or acyl; $R_3$ represents hydrogen or lower alkyl; $R_5$ represents hydrogen, lower alkyl or monocyclic carbocyclic aryl; and pharmaceutically acceptable salts thereof.

Particularly preferred are the compounds of formula IV

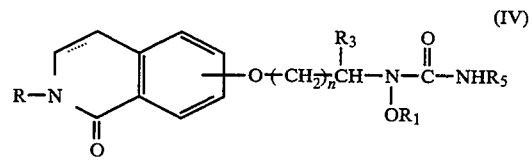

(IV)

wherein R represents biaryl-lower alkyl, carbocyclic or heterocyclic aryl-$C_1$-$C_4$-alkyl, carbocyclic or heterocyclic aryloxy-$C_1$-$C_4$-alkyl, carbocyclic aryloxyaryl-$C_1$-$C_4$-alkyl, carbocyclic aryl-$C_3$ or $C_4$-alkenyl or cyclohexyl-$C_1$-$C_4$-alkyl; n represents 1,2 or 3; $R_1$ represents hydrogen or acyl; $R_3$ represents hydrogen or $C_1$-$C_3$-alkyl; $R_5$ represents hydrogen, lower alkyl or monocyclic carbocyclic aryl; and pharmaceutically acceptable salts thereof.

Of particular interest are the compounds of formula IV wherein the chain on the benzene ring is attached at the 6- or 7-position; also compounds wherein $R_1$ represents hydrogen; also said compounds of formula IV in which dotted line is absent; and pharmaceutically acceptable salts thereof.

A preferred embodiment of the invention relates to the compounds of formula IVa

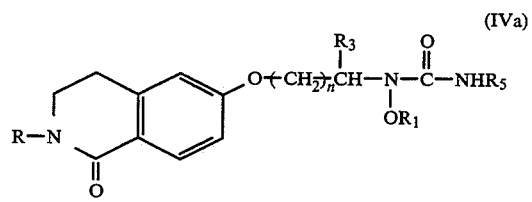

(IVa)

wherein R represents biaryl-$C_1$-$C_4$-alkyl, carbocyclic or heterocyclic aryl-$C_1$-$C_4$-alkyl, carbocyclic or heterocyclic aryloxy-$C_1$-$C_4$-alkyl, carbocyclic aryloxyaryl-$C_1$-$C_4$-alkyl, carbocyclic aryl-$C_3$ or $C_4$-alkenyl or cyclohexyl-$C_1$-$C_4$-alkyl; n represents 1,2 or 3; $R_1$ represents hydrogen or acyl; $R_3$ represents hydrogen or $C_1$-$C_3$-alkyl; $R_5$ represents hydrogen, lower alkyl or monocyclic carbocyclic aryl; and pharmaceutically acceptable salts thereof.

Further preferred are said compounds of formula IVa wherein R represents biaryl-$C_1$-$C_4$-alkyl in which biaryl represents 4-biphenylyl or 4-biphenylyl substituted by lower alkyl, halogen or trifluoromethyl; n represents 1 or 2; $R_1$ and $R_3$ represent hydrogen; $R_5$ represents hydrogen or lower alkyl; and pharmaceutically acceptable salts thereof.

A preferred embodiment of the invention also relates to the compounds of formula I wherein Z represents ethylene; Y represents CO or $SO_2$; A represents oxygen; B represents alkylene of 1 to 4 carbon atoms; R represents quinolyl-$C_1$-$C_4$-alkyl or biaryl-$C_1$-$C_4$-alkyl; Ra, $R_1$, $R_3$ and $R_4$ represent hydrogen; and $R_2$ represents amino or mono-lower alkylamino; and pharmaceutically acceptable salts thereof.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1-4 carbon atoms, advantageously 1-3 carbon atoms, and represents for example ethyl, propyl, butyl or most advantageously methyl.

A lower alkenyl group, as in lower alkenylamino, is preferably bonded on a saturated carbon. Such group preferably has 3–7 carbon atoms, advantageously 3 or 4 carbon atoms and is e.g. allyl.

A lower alkynyl group, as in lower alkynylamino, is preferably bonded on a saturated carbon. Such group preferably has 3–7 carbon atoms, advantageously 3 or 4 carbon atoms and is e.g. propargyl.

A lower alkoxy (or alkyloxy) group preferably contains 1–4 carbon atoms, advantageously 1–3 carbon atoms, and represents for example methoxy, ethoxy, propoxy or isopropoxy.

Halogen (halo) preferably represents chloro or fluoro but may also be bromo or iodo.

Aryl represents carbocyclic or heterocyclic aryl, preferably carbocyclic aryl.

Carbocyclic aryl represents monocyclic or bicyclic aryl, for example phenyl or phenyl mono- or di-substituted by one or two radicals selected from lower alkyl, lower alkoxy, halogen, cyano and trifluoromethyl; or 1- or 2-naphthyl. Preferred is phenyl or phenyl monosubstituted by halogen or trifluoromethyl.

Heterocyclic aryl represents monocyclic or bicyclic heteroaryl, for example pyridyl, quinolyl, isoquinolyl, benzothienyl, benzofuranyl, benzopyranyl, benzothiopyranyl, dihydrobenzopyranyl, dihydrobenzothiopyranyl, furanyl, pyrrolyl or thienyl, or any said radical substituted by lower alkyl or halogen. Pyridyl represents 2-, 3- or 4-pyridyl, advantageously 2- or 3-pyridyl. Thienyl represents 2- or 3-thienyl, advantageously 2-thienyl. Quinolyl represents preferably 2-, 3- or 4-quinolyl, advantageously 2-quinolyl. Isoquinolyl represents preferably 1-, 3- or 4-isoquinolyl. Benzopyranyl, benzothiopyranyl represent preferably 3-benzopyranyl or 3-benzothiopyranyl, respectively.

Carbocyclic aryl-lower alkenyl represents, e.g. for R, preferably straight-chain or branched aryl-$C_3$ or $C_4$-alkenyl in which the double bond is not bonded to nitrogen; similarly carbocyclic aryl-lower alkynyl.

Carbocyclic aryl-lower alkyl represents preferably straight chain or branched aryl-$C_1$-$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above.

Heterocyclic aryl-lower alkyl represents preferably straight chain or branched heterocyclic aryl-$C_1$-$C_4$-alkyl in which heterocyclic aryl has meaning as defined above, e.g. 2-, 3- or 4-pyridylmethyl or (2-, 3- or 4-pyridyl)-(ethyl, propyl or butyl); or 2-or 3-thienylmethyl or (2- or 3-thienyl)-(ethyl, propyl or butyl); 2-, 3- or 4-quinolylmethyl or (2-, 3- or 4-quinolyl)-(ethyl, propyl or butyl); and the like.

Biaryl is preferably carbocyclic biaryl, e.g. biphenyl, namely 2,3 or 4-biphenyl, advantageously 4-biphenyl, each optionally substituted by e.g. lower alkyl, lower alkoxy, halogen, trifluoromethyl or cyano.

Similarly the terms carbocyclic aryl, heterocyclic aryl, lower alkyl, lower alkenyl, lower alkynyl have meaning as defined above in any groups in which such appear, e.g. aryloxy, aryl-lower alkoxy and the like.

Acyl is preferably optionally substituted lower alkanoyl or aroyl.

Optionally substituted lower alkanoyl represents preferably $C_2$-$C_4$-alkanoyl such as acetyl or propionyl, or $C_2$-$C_4$-alkanoyl substituted by lower alkoxycarbonyl.

Aroyl represents preferably benzoyl or benzoyl mono- or di-substituted by one or two radicals selected from lower alkyl, lower alkoxy, halogen, cyano and trifluoromethyl; or 1- or 2-naphthoyl.

Lower alkoxycarbonyl represents preferably $C_1$-$C_4$-alkoxycarbonyl, e.g. ethoxy.

Substituted amino represents preferably mono- or di-lower alkylamino or mono-carbocyclic arylamino.

$C_3$-$C_7$-Cycloalkyl represents cyclopropyl, cyclobutyl, cyclopentyl, cyclohexyl or cycloheptyl, preferably cyclopropyl, cyclohexyl or cyclopentyl.

Aryl-$C_3$-$C_7$-cycloalkyl-lower alkyl represents for example 2-phenylcyclopropylmethyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by $C_1$-$C_3$-alkyl (advantageously methyl) or disubstituted on the same or different carbon atoms by $C_1$-$C_3$-alkyl (advantageously methyl), the total number of carbon atoms being up to and including 7.

Lower alkenylene represents straight chain or branched alkenylene of 2 to 7 carbon atoms and represents preferably straight chain alkenylene of 2 to 4 carbon atoms, e.g. vinylene, propenylene, butenylene or said chain mono-substituted by $C_1$-$C_3$-alkyl (e.g. methyl) or disubstituted on the same or different carbon atoms by $C_1$-$C_3$-alkyl (e.g. methyl), the total number of carbon atoms being up to and including 7.

Pharmaceutically acceptable salts of the acidic compounds of the invention (provided that $R_1$ represents hydrogen) are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the invention exhibit valuable pharmacological properties in mammals, and are particularly useful as selective 5-lipoxygenase inhibitors for the treatment of e.g. inflammatory, allergic and ischemic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-8}$ molar concentrations. The dosage in vivo may range, depending on the route of administration, between about 0.05 and 30 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocytechemoattractant, smooth muscle-constricting and vascular permeability-enhancing properties. LTB$_4$ is among the most potent leukocyte chemotactic agents known. LTC$_4$, LTD$_4$ and LTE$_4$ are components of the "slow-reacting substance of anaphylaxis" (SRS-A) and are potent inducers of broncho-constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, inhibition of 5-lipoxygenase will suppress biosynthesis of leukotrienes in leukocytes and various organ systems.

Beneficial effects are evaluated in pharmacological tests generally known in the art, e.g. as illustrated herein.

5-Lipoxygenase inhibition is determined e.g. by measuring the percent inhibition of the synthesis of 5-HETE [(5S)-5-hydroxy-6,8,11,14-eicosa-tetraenoic acid] and leukotriene B$_4$ (LTB$_4$,5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (Nature 287: 51, 1980) to measure the formation of 5-HETE and LTB$_4$-like products from $^{14}$C-arachidonic acid. IC$_{50}$ values are determined graphically as the concentration of test compound at which the synthesis of 5-HETE and LTB$_4$-like products is reduced to 50% of their respective control values.

The inhibition of LTB$_4$ formation can also be determined in vitro in whole blood from dogs. One ml samples of blood are preincubated at 37° C. for 5 minutes with the desired concentration of test compound added as a solution in 10 microliters of dimethylsulfoxide. LTB$_4$ synthesis is then stimulated by the addition of A-23187 and N-formyl-met-leu-phe (f-MLP). The amount of LTB$_4$ is measured in the separated plasma fraction by radioimmunoassay. IC$_{50}$ values are determined graphically as the concentration of test compound causing 50% inhibition of LTB$_4$ formation seen in control whole blood.

Furthermore, the inhibition of 5-lipoxygenase is determined after oral or i.v. administration to rats or dogs by measuring ex vivo in whole blood the decrease of A-23187-stimulated LTB$_4$ formation as compared to non-treated control animals.

Antiinflammatory activity can be demonstrated by measuring the inhibition of the edema and inhibition of the influx of polymorphonuclear (PMN's) and mononuclear leukocytes (monocytes and macrophages) after oral administration in the rat model in which pleurisy is first induced by injecting carrageenin into the pleural cavity, e.g. according to A. P. Almeida et al., J. Pharmacol. Exp. Therap. 214, 74 (1980), in particular during the late phase of the carrageenan-induced pleurisy.

Bronchial effects such as anti-asthmatic activity, can be demonstrated in the antigen-induced guinea pig bronchoconstriction test, e.g. as described by Anderson et al, Br. J. Pharmacol. 1983, 78, 67–74.

The trinitrobenzenesulfonic acid-induced chronic colitis test in the rat, e.g. as described by Wallace et al, Gastroenterology 1989, 96, 29–36, can be used to evaluate compounds for effects indicative of utility in inflammatory bowel diseases.

The arachidonic acid-induced mouse ear edema test, e.g. as described by Young et al, J. Invest. Dermatol. 1984, 82, 367–371 can be used to evaluate compounds for effects indicative of utility in dermatological disorders such as psoriasis.

Illustrative of the invention, the compound of example 1(f), 2-(3-phenylpropyl)-6-[2(N-aminocarbonyl-N-hydroxyamino)ethoxy]-1,2,3,4-tetrahydroisoquinolin-1-one, inhibits the formation of 5-HETE [(5S)-5-hydroxy-6,8,11,14-eicosa-tetraenoic acid] and leukotriene B$_4$ (LTB$_4$, 5,12-dihydroxy-6,8,10,14-eicosatetraenoic acid) in A-23187-stimulated guinea pig polymorphonuclear leukocytes, at an IC$_{50}$ of about 0.5 micromolar. Said compound also causes significant inhibition of LTB$_4$ formation as determined ex vivo when administered at a dose of about 1.0 mg/kg p.o. to the dog.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders (such as asthma), dermatological allergies and inflammatory disorders (such as psoriasis), also arthritic disorders (such as rheumatoid arthritis and osteoarthritis), ocular allergies and inflammatory disorders, gastrointestinal inflammatory disorders (such as inflammatory bowel diseases), as well as ischemic conditions (such as in myocardial infraction).

The compounds of the invention can be prepared by the following synthetic processes which comprise:

(a) condensing a hydroxylamine derivative of formula V

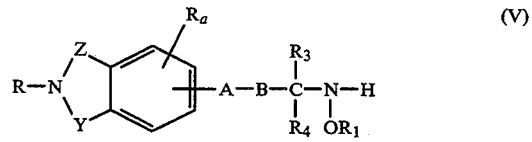

wherein R, R$_1$, R$_3$, R$_4$, R$_a$, A, B, Z and Y have meaning as defined hereinabove, with a compound of formula VI

R$_2$'—COOH  (VI)

in the presence of a condensing agent, or with a reactive functional derivative thereof, wherein R$_2$' represents lower alkyl, lower alkoxycarbonyl-lower alkyl, C$_3$–C$_7$-cycloalkyl, carbocyclic or heterocyclic aryl, carbocyclic or heterocyclic aryl-lower alkyl, C$_3$–C$_7$-cycloalkyl-lower alkyl or all-lower alkylamino, to obtain said compounds of formula I wherein X represents 0 and R$_2$ corresponds to R$_2$'; or (b) condensing a compound of the formula V above with phosgene or thiophosgene, followed by an amine of the formula VII

R$_2$''—H  (VII)

wherein R$_2$'' represents amino, mono- or all-lower alkylamino, lower alkenylamino, lower alkynylamino, carbocyclic or heterocyclic arylamino, C$_3$–C$_7$-cycloalkylamino, carbocyclic or heterocyclic aryl-lower alkylamino, C$_3$–C$_7$-cycloalkyl-lower alkylamino, or lower alkoxycarbonyl-lower alkylamino, to obtain said compounds of formula I wherein $R_2$ corresponds to $R_2''$; or (c) condensing a compound of formula V above with an isocyanate or isothiocyanate of the formula VIII $$R_5-N=C=X \qquad (VIII)$$

wherein X represents O or S; $R_5$ represents a protecting group (such as tri-lower alkyl silyl), or $R_5$ represents lower alkyl, lower alkenyl, lower alkynyl, carbocyclic or heterocyclic aryl, $C_3$-$C_7$-cycloalkyl, $C_3$-$C_7$-cycloalkyl-lower alkyl, carbocyclic or heterocyclic aryl-lower alkyl, or lower alkoxycarbonyl-lower alkyl; and if required removing the protecting group, e.g. the tri-lower alkyl silyl group when $R_5$ represents e.g. the tri-lower alkyl silyl protecting group, to obtain said compounds of formula I wherein $R_2$ corresponds to $R_5NH$ in which $R_5$ represents hydrogen or other groups as defined above for $R_5$.

In the above cited processes, the said process is carried out while, if necessary, temporarily protecting any interfering reactive group(s), and then liberating the resulting compound of the invention: and, if required or desired, a resulting compound of the invention is convened into another compound of the invention, and/or, if desired, a resulting free compound is convened into a salt or a resulting salt is convened into a free compound or into another salt; and/or a mixture of isomers or racemates obtained is separated into the single isomers or racemates; and/or, if desired, a racemate is resolved into the optical antipodes.

In starting compounds and intermediates which are convened to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, N.Y., 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

Also, a reactive esterified derivative of an alcohol in any of the processes cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halo, for example chloro, bromo or iodo, or aliphatically or aromatically substituted sulfonyloxy, for example methanesulfonyloxy, 4-methylbenzenesulfonyloxy (tosyloxy) or trifluoromethylsulfonyloxy.

The above processes for the synthesis of compounds of the invention can be carried out according to methodology generally known in the art for the preparation of hydroxylamine derivatives.

The synthesis according to process (a) involving the condensation of carboxylic acid of formula VI or a reactive functional derivative thereof with a hydroxylamine derivative of formula V (optionally hydroxy-protected when $R_1$ represents hydrogen) can be carried out in the presence of a condensing agent, e.g. diethyl phosphonocyanidate, 1,1'-carbonyldiimidazole or carbodiimides, e.g. dicyclohexylcarbodiimide, in an inert polar solvent, such as dimethylformamide or dichloromethane.

The synthesis according to process (a) involving the condensation of a reactive functional derivative of an acid of formula VI as described above, e.g. an acid chloride or mixed anhydride, with an optionally hydroxy protected hydroxylamine derivative of formula V, or a salt thereof, in the presence of a base such as triethylamine can be carried out at a temperature ranging preferably from about $-78°$ C. to $+75°$ C., in an inert organic solvent such as dichloromethane or toluene.

In the case of acylation of the compounds of formula V wherein $R_1$ represents hydrogen, e.g. with 2 mole equivalents or excess of a functional derivative of a compound of formula VI, the N,O-bis-acylated compounds of formula I, namely those wherein $R_1$ represents $COR_2$, are obtained. The N,O-diacylated compounds of formula I, e.g. wherein $R_2$ represents lower alkyl or di-lower alkylamino and $R_1$ represents the corresponding $COR_2$ group, can be selectively O-deacylated under basic conditions, e.g., with aqueous lithium hydroxide to yield the corresponding compounds of formula I wherein $R_1$ represents hydrogen.

Processes (b) and (c) are directed to the preparation of urea derivatives, the compounds of formula I wherein $R_2$ represents amino or substituted amino, from hydroxylamines of formula V.

The preparation according to process (b) can be carried out by reacting the hydroxylamine derivative of formula V, optionally in hydroxy-protected form, with phosgene or thiophosgene in an inert solvent such as toluene followed by condensation with the appropriate amine at a temperature of about $-25°$ C. to $+150°$ C.

The preparation according to process (c) involves the condensation of a hydroxylamine of formula V or a salt thereof, optionally in hydroxy-protected form, with e.g. the isocyanate in an inert solvent such as toluene, acetonitrile or dioxane at a temperature ranging from $-10°$ C. to reflux temperature.

In the case of reaction of compounds of formula V wherein $R_1$ represents hydrogen with 2 moles of a compound of formula VIII, compounds of formula I wherein $R_1$ represents e.g. $COR_2$ can be obtained.

Protected forms of hydroxylamines of formula V in the above processes are those wherein the hydroxy group is protected for example as a benzyl ether or tetrahydropyranyl ether. Removal of said protecting groups is carried out according to methods well known in the art, e.g. hydrogenolysis or acid hydrolysis, respectively.

The carboxylic acids of VI and reactive derivatives thereof are known in the art or can be prepared according to methods well-known in the art; similarly the amines of formula VII, and the isocyanates and isothiocyanates of formula VIII are known in the art or can be prepared according to methods well-known in the art.

The intermediates leading to starting materials of formula V are hereafter described for compounds wherein $R_a$ represents hydrogen. However, such is not to be construed as any limitation on the compounds of the invention as defined herein since methods are applicable to compounds wherein $R_a$ is other than hydrogen.

The starting hydroxylamine derivatives of formula V may be prepared from a corresponding reactive derivative of an alcohol of formula IX

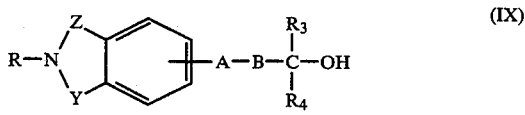

wherein R, $R_3$, $R_4$, A, B, Y and Z have meaning as defined hereinabove, such as the corresponding bromide, iodide, tosylate or mesylate derivative, by condensing such with a protected hydroxylamine derivative, e.g. N,O-bis(tert-butoxycarbonyl)hydroxylamine, followed by deprotection, e.g. with trifluoroacetic acid.

Alternatively hydroxylamines of formula V wherein at least one of $R_3$ or $R_4$ represents hydrogen can be prepared from the corresponding aldehyde or ketone of formula X

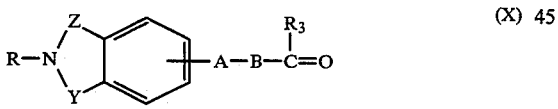

wherein R, $R_3$, A, B, Z and Y have meaning as previously defined, by first convening said aldehyde or ketone to the oxime with e.g. hydroxylamine hydrochloride according to known methods, followed by reduction to the hydroxylamine with e.g. borane-pyridine complex or sodium cyanoborohydride in acidic medium.

The alcohols of formula IX may be prepared from corresponding carboxylic acids and derivatives, aldehydes or ketones by methods well-known in the art, e.g. using an appropriate reducing agent, or by condensing with e.g. an alkyl Grignard reagent corresponding to $R_3$ and/or $R_4$ when $R_3$ and $R_4$ do not represent hydrogen.

The starting aldehydes or ketones of formula X for compounds wherein A is oxygen or sulfur can be prepared e.g. by condensing an appropriately substituted phenol or thiophenol of formula XI

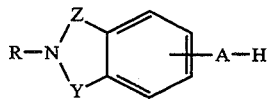

wherein R, Z and Y have meaning as defined above, and A represents oxygen or sulfur, (a) with a reactive esterified derivative of a terminal alkenyl alcohol of the formula XII

wherein $R_3$ represents hydrogen or lower alkyl and B represents lower alkylene, such as the halide or alkylsulfonyloxy derivative thereof, in the presence of a base, such as potassium carbonate, to yield the terminal alkenyl derivative which is then treated with ozone to obtain the corresponding aldehyde or ketone of formula X wherein A represents sulfur or oxygen and B represents lower alkylene; or (b) with a reactive esterified derivative of a protected aldehyde or ketone of the formula XII

wherein $R_3$ represents hydrogen or lower alkyl and B represents lower alkylene, and wherein the aldehyde or ketone function is protected in form of an acetal or ketal, such as the halide or alkylsulfonyloxy derivative thereof, in the presence of a base such as potassium carbonate or cesium carbonate, and liberating the ketone or aldehyde of formula X from the resulting ketal or acetal by treatment with aqueous acid.

The starting aldehydes or ketones of formula X wherein A represents a direct bond and B represents lower alkenylene, with the double bond being directly adjacent to the ring system, can be prepared by condensing a compound of the formula XIV

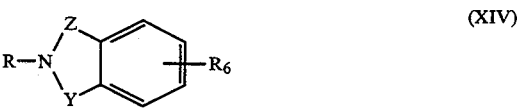

wherein R, Z and Y have meaning as defined above and $R_6$ represents e.g. bromo or trifluoromethylsulfonyloxy, with an unsaturated aldehyde or ketone corresponding to the fragment $B—COR_3$ in formula X (wherein B represents terminal lower alkenyl and $R_3$ represents hydrogen or lower alkyl) in which the carbonyl function is protected in form of an acetal or ketal, for example acrolein diethyl acetal, under conditions of a Heck reaction, e.g. in the presence of palladium acetate, triphenylphosphine and triethylamine, and subsequently liberating the resulting ketone or aldehyde of formula X by treatment with aqueous acid.

The corresponding starting materials of formula X wherein A represents a direct bond and B represents lower alkylene can be prepared by hydrogenation of the corresponding compounds of formula X wherein B represents lower alkenylene.

The starting materials of formula XI and of formula XIV or precursors thereto wherein Y represents CO and Z represents ethylene or 1,3-propylene optionally substituted by lower alkyl are either known or can be prepared according to methods known in the art, e.g. by ring expansion of a corresponding indanone or tetralone to the lactam.

For example, Schmidt reaction, e.g. with sodium azide in methanesulfonic acid, on a ketone of the formula XV

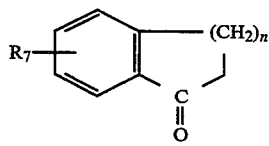
(XV)

wherein $R_7$ represents e.g. halo, lower alkoxy or benzyloxy, and n represents 1 or 2 yields a compound of formula XVI

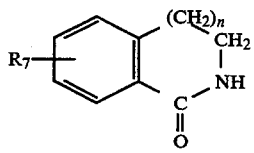
(XVI)

wherein $R_7$ and n have meaning as defined above for compounds of formula XV. Subsequent N-substitution in the presence of a strong base such as sodium hydride with a reactive esterified derivative of R—OH, and in case $R_7$ represents e.g. lower alkoxy or benzyloxy, later deprotection to $R_7$ being hydroxy, according to known methods (e.g. hydrogenation or $BBr_3$), results in a starting material of formula XI or XIV wherein Y represents CO.

A lactam of formula XVI can also be prepared by Beckmann rearrangement of the oxime of a ketone of formula XV in the presence of e.g. phosphorous pentoxide and methanesulfonic acid.

The ketones of formula XV are known in the an or can be prepared according to methodology known in the art, e.g. by Friedel-Crafts cyclization of the appropriately substituted phenylalkanoic acid e.g. with a mixture of phosphorus oxychloride and phosphorus pentoxide.

The lactam derivatives of formula XVI and N-substituted derivatives thereof wherein n represents zero, 1 or 2, and $R_7$ represents e.g. halo, lower alkoxy or benzyloxy can also be prepared by cyclization of the corresponding urethane of the formula XVII

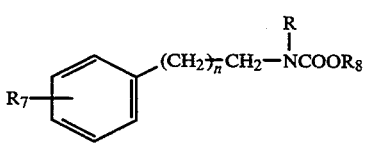
(XVII)

wherein R has meaning as previously defined; $R_8$ represents e.g. lower alkyl; n is zero, 1 or 2; and $R_7$ is halo, lower alkoxy or benzyloxy, preferably located at the meta position, using a Lewis acid such as polyphosphoric acid/polyphosphate ester, similarly to methodology described in J. Her. Chem. 13, 1329 (1976). The starting urethanes are prepared by treating an appropriate $R_7$-substituted phenyl-$C_1$-$C_3$-alkylamine with a lower alkyl ester of chloroformic acid.

Another method for the preparation of lactam intermediates of formula XVI (wherein n represents zero, 1 or 2) involves the cyclization of an appropriately substituted ortho (amino-methyl, amino-ethyl or amino- propyl)-benzoic acid derivative, which can in turn be obtained by reduction of the corresponding ortho-(cyano, cyanomethyl or cyanoethyl)-benzoic acid derivative.

A method for the preparation of the N-substituted derivatives of the lactams of formula XVI wherein n represents zero (isoindolones, 1-oxo-1,3-dihydrobenzo[c]-pyrroles) involves the treatment of an appropriately substituted benzamide first with an alkyllithium reagent, e.g. n-butyl lithium, followed by condensation with dimethylformamide to yield the correspondingly substituted 3-hydroxyisoindolone which is reduced e.g. by catalytic hydrogenation to the isoindolone.

The starting materials of formula XI or XIV wherein Y represents CO and Z represents methylene may also be prepared by selective reduction of the corresponding phthalimides under conditions known in the art, such as with lithium aluminum hydride or by catalytic hydrogenation.

The starting materials of formula XI and XIV wherein Y represents CO and Z represents vinylene can be prepared by heating a correspondingly substituted cinnamoyl azide, e.g. in the presence of iodine in a high boiling solvent such as dichlorobenzene, to obtain a corresponding substituted isocarbostyril derivative of formula XVIa

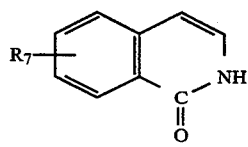
(XVIa)

wherein $R_7{'}$ represents halo, or $R_7{'}$ represents e.g. lower alkoxy or benzyloxy in which case such can be converted to a compound of formula XI wherein Z represents vinylene, A represents oxygen and Y represents CO.

The starting materials wherein Y represents $SO_2$ can be prepared by methods generally known in the art.

For example, compounds of formula XI wherein Y is $SO_2$ and Z is $C_1$-$C_3$-alkylene can be prepared as follows:

An ester of a compound of formula XVIII

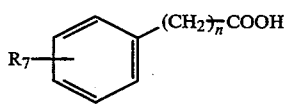
(XVIII)

wherein $R_7$ represents e.g. lower alkoxy or benzyloxy, preferably located at the meta position, and n is 0, 1 or 2, is treated with chlorosulfonic acid followed by ammonia or $RNH_2$ to obtain an ester of a compound of the formula XIX

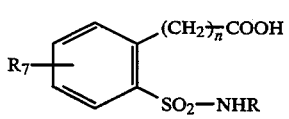
(XIX)

Cyclization under basic conditions with a strong base, e.g. sodium methoxide in toluene, yields a compound of the formula XX

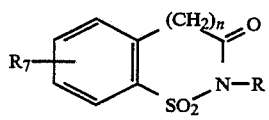

wherein $R_7$ represents lower alkoxy or benzyloxy and n and R having meaning as defined above. The amide carbonyl function is then reduced with e.g. diborane and converted to the corresponding phenol of formula XI wherein A represents oxygen.

Appropriate N-unsubstituted intermediates (wherein R represents hydrogen) can be converted to the corresponding N-substituted compounds by treatment with a reactive esterified derivative of R—OH in the presence of a strong base such as sodium hydride, according to methodology well-known in the art, and described herein.

The alcohols (ROH) are either known in the literature or can be prepared according to methods known in the art. For example, where R represents biaryl-lower alkyl, such alcohols can be prepared by reduction of the corresponding carboxylic acids or esters. The acids or esters can in turn be prepared by a cross-coupling reaction of e.g. an optionally substituted phenylboronic acid with e.g. a halo or (alkyl or aryl)-sulfonyloxy substituted benzoic or phenylalkanoic acid ester under conditions known in the art.

The above-mentioned chemical reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or superatmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

Compounds of the invention can also be converted into each other according to methods generally known per se and/or illustrated herein.

For example, compounds of formula I wherein X represents oxygen e.g. wherein $R_1$ represents acyl, can be converted to the corresponding compounds wherein X represents sulfur by reaction with e.g. Lawesson's reagent. Compounds of formula I, e.g. wherein B represents alkenylene or Z represents vinylene can be converted to the corresponding compounds of formula I wherein B represents alkylene or Z represents ethylene by hydrogenation of the double bond using e.g. palladium on charcoal as catalyst.

Compounds of formula I wherein $R_1$ represents hydrogen can be converted to the corresponding compounds wherein $R_1$ represents acyl by treatment with the appropriate acylating agent, e.g. the acyl halide, for example acetyl chloride.

Conversely compounds of formula I wherein $R_1$ represents acyl can be hydrolyzed to the corresponding compounds wherein $R_1$ represents hydrogen, e.g. with aqueous base such as lithium hydroxide or sodium hydroxide.

The invention also relates to any novel starting materials and processes for their manufacture.

Depending on the choice of starting materials and methods, the new compounds may be in the form of one of the possible isomers or mixtures thereof, for example, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids (wherein $R_1$ represents hydrogen) can thus be resolved into their optical antipodes e,g. by fractional crystallization of d- or l-(alpha-methylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be convened into the free compounds by treatment with acids. These or other salts can also be used for purification of the compounds obtained.

Compounds of the invention having basic groups can be convened into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$-)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$-)alkane- or arylsulfonic acids which are unsubstituted or substituted, for example, by halogen, for example methanesulfonic acid. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit lipoxygenase, in particular 5-lipoxygenase, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The pharmaceutical formulations contain an effective lipoxygenase inhibiting amount of a compound of the invention as defined above either alone, or in combination with another therapeutic agent selected from e.g. an anti-inflammatory agent with cyclooxygenase inhibiting activity, a leukotriene receptor antagonist, a thromboxane synthetase inhibitor, a thromboxane receptor antagonist, an antihistamine, a platelet activating factor (PAF) antagonist and a serotonin receptor antagonist, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

Examples of leukotriene antagonists are LY-223982, SC-41930, ICI-204219, L-660711, and the like.

Examples of thromboxane synthetase inhibitors are ozagrel (OKY-046), pirmagrel (CGS 13080), CGS 12970, CGS 15435 and the like.

Examples of thromboxane receptor antagonists are sulotroban, ICI- 192605, GR-32191, SQ-30741, L-655240 and the like.

Examples of combined thromboxane synthetase inhibitors/thromboxane receptor antagonists are CGS 22652 (U.S. Pat. No. 5,025,025) and the like.

Examples of antihistaminic agents are astemizole, loratidine, terfanidine, chlorpheniramine and the like.

Examples of platelet activating factor antagonists are BN-52063, WEB-2086, CV-3988, RP-48740, L-652731 and the like. Examples of serotonin antagonists are ketanserin, cinanserin, irindalone and the like.

In conjunction with another active ingredient, a compound of the invention may be administered either simultaneously, before or after the other active ingredient, either separately by the same or different route of administration or together in the same pharmaceutical formulation.

The invention further particularly relates to a method of inhibiting 5-lipoxygenase activity in mammals including man, and of treating diseases and conditions responsive thereto, particularly inflammatory and allergic conditions, which comprises administering to a mammal in need thereof an effective lipoxygenase inhibiting amount of a compound of the invention or of a pharmaceutical composition comprising a said compound in combination with one or more pharmaceutically acceptable carriers.

Conditions and diseases responsive to the inhibition of lipoxygenase include:

a) allergic conditions such as hay fever (allergic rhinitis), skin allergies, allergic bowel diseases (incl. coeliac disease), allergic eye conditions such as allergic conjunctivitis;

b) inflammatory conditions such as inflammatory bowel disease, irritable bowel syndrome, mucous colitis, ulcerative colitis, Crohn's disease, gastritis, esophagitis, hepatitis;

c) cardiovascular conditions such as myocardial ischemia, cerebral ischemia, atherosclerosis, angina, and renal ischemia;

d) pulmonary conditions such as extrinsic and intrinsic asthma, bronchitis, cystic fibrosis;

e) arthritic conditions such as rheumatoid arthritis, rheumatoid spondylitis, gouty arthritis, osteoarthritis and the like;

f) cutaneous disorders such as psoriasis, eczema and dermatitis;

g) multiple sclerosis, arteriosclerosis of various etiology and shock such as endotoxin shock; and h) tumor metastasis.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably be-

EXAMPLE 1

(a) To a stirred solution of 2-[3-(4-fluorophenyl)-propyl]-6-[2-(N-hydroxyamino)ethoxy]-1-oxo-1,2,3,4-tetrahydroisoquinoline (3.0 g, 8.4 mmol) in dioxane (100 mL) is added trimethylsilyl isocyanate (1.06 g, 9.2 mmol). The reaction is stirred at room temperature for 24 hours and subsequently poured into H$_2$O (350 mL). The resulting suspension is extracted with EtOAc (1×500 mL) and the organic phase washed with 2M HCl (1×250 mL), H$_2$O (5×500 mL), saturated NaCl solution (2×500 mL), dried over MgSO$_4$ and concentrated in vacuo. The resulting material is triturated with hexanes, and recrystallized from EtOAc to give 2-[3-(4-fluorophenyl)-propyl]-6-[2-(N-aminocarbonyl-N-hydroxyamino)ethoxy]-1-oxo-1,2,3,4-tetrahydroisoquinoline, m.p. 138°–140°.

The starting material is prepared as follows:

5-Methoxy-1-indanone 1 (30 g, 185 mmol) is dissolved in CH$_3$SO$_3$H (96 mL) and CH$_2$Cl$_2$ (100 mL), NaN$_3$ (24 g, 370 mmol) is then added in portions over a ½ hour period. After 2 hours the reaction mixture is cooled to 0° and is subsequently neutralized with 5N NaOH solution (200 mL) and saturated NaHCO$_3$ solution. The resulting mixture is extracted with EtOAc (3×200 mL). The combined organic phases are washed with saturated NaCl solution (3×200 mL), dried over Na$_2$SO$_4$ and concentrated in vacuo. The resulting brown solid is washed with hexanes (2×100 mL) to give 6-methoxy-1-oxo-1,2,3,4-tetrahydroisoquinoline as a tan solid, m.p. 128°–130°.

To a solution of 6-methoxy-1-oxo-1,2,3,4-tetrahydroisoquinoline (31.3 g, 177 mmol) in CH$_2$Cl$_2$ (300 mL) at −78° is added BBr$_3$ (33.4 mL, 353 mmol). The reaction mixture is allowed to come to ambient temperature and is stirred for 12 hours. After this time the reaction mixture is cooled to 0° and is subsequently neutralized with 5N NaOH (150 mL) solution and saturated NaHCO$_3$ solution. The resulting precipitate is extracted with hot acetone (4×500 mL) and the combined organics are concentrated in vacuo to give 6-hydroxy-1-oxo-1,2,3,4-tetrahydroisoquinoline.

To a solution of 6-hydroxy-1-oxo-1,2,3,4-tetrahydroisoquinoline (23.8 g, 146 mmol) in acetone (350 mL) is added K$_2$CO$_3$ (34.6 g, 219 mmol) and allyl bromide (19.3 g, 161 mmol). The reaction mixture is then heated to reflux for 24 hours. After this time the solution is filtered and subsequently concentrated in vacuo. The resulting material is washed with hexanes (1×200 mL) and Et$_2$O (1×100 mL) to give 6-allyloxy-1,2,3,4-tetrahydroisoquinolin-1-one as a tan solid, m.p. 105°–107°.

To a solution of 6-allyloxy-1-oxo-1,2,3,4-tetrahydroisoquinoline (10.6 g, 52 mmol) and 1-bromo-3-(4-fluorophenyl)-propane (17 g, 78 mmol) and KI (430 mg, 2.6 mmol) in dimethyl formamide (DMF) (125 mL) is added NaH (3.1 g, 78 mmol). After 4 hours the reaction mixture is poured into H$_2$O (500 mL) and the resulting suspension is extracted with EtOAc (3×300 mL). The combined organic extracts are washed with H$_2$O (5×200 mL), saturated NaCl solution (2×200 mL), dried over MgSO$_4$ and concentrated in vacuo. The residue is chromatographed (silica gel, 1:1 EtOAc/hexane) to yield 2-[3-(4-fluorophenyl)-propyl]-6-allyloxy-1-oxo-1,2,3,4-tetrahydroisoquinoline as a brown oil.

2-[3-(4-Fluorophenyl)-propyl]-6-allyloxy-1-oxo-1,2,3,4-tetrahydroisoquinoline (3.24 g, 9.5 mmol) is dissolved in CH$_2$Cl$_2$/MeOH (1:1, 200 mL), the solution cooled to −78° and ozone is bubbled through the reaction flask until an excess is indicated by the persistence of a dark blue color. Nitrogen is then bubbled through the mixture to purge excess ozone. Dimethyl sulfide (1.77 g, 28.5 mmol) is added to the reaction, and the resulting solution is allowed to warm to room temperature. The solvent is removed in vacuo, and the resulting α-{2-[3-(4-fluorophenyl)-propyl]-1-oxo-1,2,3,4-tetrahydroisoquinolin-6-yloxy}-acetaldehyde is used without further purification in the next step.

To a solution of the aldehyde (approximately 9.5 mmol) and NH$_2$OH.HCl (0.79 g, 11.4 mmol) in EtOH (100 mL) is added pyridine (50 mL). The resulting mixture is stirred at room temperature for 24 hours. After this time the reaction is poured into H$_2$O (500 mL), and the aqueous phase is extracted with EtOAc (1×500 mL). The organic phase is washed with 2N HC; (3×500 mL), H$_2$O (1×500 mL), saturated NaHCO$_3$ solution (1×500 mL), saturated NaCl solution (2×500 mL), dried over MgSO$_4$ and the solution is concentrated in vacuo. The resulting oxime is used without further purification for the next reaction.

To a solution of the oxime (3.13 g, 8.8 mmol) in glacial AcOH (10 mL) and CH$_2$CL$_2$ (20 ml) at 0° is added NaCNBH$_3$ (0.66 g, 10.6 mmol). The cooling bath is removed and the reaction mixture is stirred for 10 minutes. After this time the solution is recooled to 0° and subsequently neutralized with 5N NaOH and saturated NaHCO$_3$ solutions. The resulting suspension is then extracted with EtOAc (1×500 mL). The organic phase is washed with saturated NaHCO$_3$ solution (2×250 mL), saturated NaCl solution (2×500 mL), dried over MgSO$_4$ and concentrated in vacuo. The resulting 2-[3-(4-fluorophenyl)-propyl]-6-[2-(-N-hydroxyamino)ethoxy]-1-oxo-1,2,3,4-tetrahydroisoquinoline is used without further purification.

Similarly prepared are:

(b) 2-benzyl-6-[2-(N-aminocarbonyl-N-hydroxyamino)ethoxy]-1-oxo-1,2,3,4-tetrahydroisoquinoline, m.p. 130°–131°;

(c) 2-(4-fluorobenzyl)-6-[2-(N-aminocarbonyl-N-hydroxyamino)ethoxy]-1-oxo-1,2,3,4-tetrahydroisoquinoline, m.p. 138°–140°;

(d) 2-(3-fluorobenzyl)-6-[2-(N-aminocarbonyl-N-hydroxyamino)ethoxy]-1-oxo-1,2,3,4-tetrahydroisoquinoline, m.p. 123°–124°;

(e) 2-cyclohexylmethyl-6-[2-(N-aminocarbonyl-N-hydroxyamino)ethoxy]-1-oxo-1,2,3,4-tetrahydroisoquinoline, m.p. 182°–183°;

(f) 2-(3-phenylpropyl)-6-[2-(N-aminocarbonyl-N-hydroxyamino)ethoxy]-1-oxo-1,2,3,4-tetrahydroisoquinoline, m.p. 138°–139°;

(g) 2-(3-cyclohexylpropyl)-6-[2-(N-aminocarbonyl-N-hydroxyamino)ethoxy]-1-oxo-1,2,3,4-tetrahydroisoquinoline, m.p. 140°–142°;

(h) 2-[3-(3-fluorophenyl)-propyl]-6-[2-(N-aminocarbonyl-N-hydroxyamino)ethoxy]-1-oxo-1,2,3,4-tetrahydroisoquinoline, m.p. 123°–128°;

(i) 2-[3-(2-fluorophenyl)-propyl]-6-[2-(N-aminocarbonyl-N-hydroxyamino)ethoxy]-1-oxo-1,2,3,4-tetrahydroisoquinoline, m.p. 141°–145°;

(j) 2-[3-(4-chlorophenyl)-propyl]-6-[2-(N-aminocarbonyl-N-hydroxyamino)ethoxy]-1-oxo-1,2,3,4-tetrahydroisoquinoline, m.p. 157°–158°;

(k) 2-[3-(3-chlorophenyl)-propyl]-6-[2-(N-aminocarbonyl-N-hydroxyamino)ethoxy]-1-oxo-1,2,3,4-tetrahydroisoquinoline, m.p. 85°–87°;

(l) 2-[3-(4-methoxyphenyl)-propyl]-6-[2-(N-aminocarbonyl-N-hydroxyamino)ethoxy]-1-oxo-1,2,3,4-tetrahydroisoquinoline. m.p. 130°–134°:

(m) 2-[3-(3-methoxyphenyl)-propyl]-6-[2-(N-aminocarbonyl-N-hydroxyamino)ethoxy]-1-oxo-1,2,3,4-tetrahydroisoquinoline, m.p. 135°–137°;

(n) 2-[3-(2-methoxyphenyl)-propyl]-6-[2-(N-aminocarbonyl-N-hydroxyamino)ethoxy]-1-oxo-1,2,3,4-tetrahydroisoquinoline, m.p. 135°–137°;

(o) 2-[3-(4-tolyl)-propyl]-6-[2-(N-aminocarbonyl-N-hydroxyamino)ethoxy]-1-oxo-1,2,3,4-tetrahydroisoquinoline, m.p. 142°–146°;

(p) 2-[3-(4-isopropylphenyl)-propyl]-6-[2-(N-aminocarbonyl-N-hydroxyamino)ethoxy]-1-oxo-1,2,3,4-tetrahydroisoquinoline, m.p. 142°–146°;

(q) 2-(2-phenoxyethyl)-6-[2-(N-aminocarbonyl-N-hydroxyamino)ethoxy]-1-oxo-1,2,3,4-tetrahydroisoquinoline, m.p. 158°–159°;

(r) 2-[(2-methoxyphenyl)-ethyl]-6-[2-(N-aminocarbonyl-N-hydroxyamino)ethoxy]-1-oxo-1,2,3,4-tetrahydroisoquinoline, m.p. 153°–154°;

(s) 2-(4-phenylbutyl)-6-[2-(N-aminocarbonyl-N-hydroxyamino)ethoxy]-1-oxo-1,2,3,4-tetrahydroisoquinoline, m.p. 46°–50°;

(t) 2-[4-(4-fluorophenyl)-butyl]-6-[2-(N-aminocarbonyl-N-hydroxyamino)ethoxy]-1-oxo-1,2,3,4-tetrahydroisoquinoline, m.p. 156°–159°;

(u) 2-(3-phenoxypropyl)-6-[2-(N-aminocarbonyl-N-hydroxyamino)ethoxyl]-1-oxo-1,2,3,4-tetrahydroisoquinoline, m.p. 166°–169°;

(v) 2-(5-phenylpentyl)-6-[2-(N-aminocarbonyl-N-hydroxyamino)ethoxy]-1-oxo-1,2,3,4-tetrahydroisoquinoline, m.p. 122°–128°;

(w) 2-[3-(3-bromophenyl)-propyl]-6-[2-(N-aminocarbonyl-N-hydroxyamino)ethoxy]-1-oxo-1,2,3,4-tetrahydroisoquinoline, m.p. 95°–97°;

(x) 2-[3-(3,4-difluorophenyl)-propyl]-6-[2-(N-aminocarbonyl-N-hydroxy)amino)ethoxy]-1-oxo-1,2,3,4-tetrahydroisoquinoline, m.p. 133°–135°;

(y) 2-[3-(3,5-difluorophenyl)-propyl]-6-[2-(N-aminocarbonyl-N-hydroxyamino)ethoxy]-1-oxo-1,2,3,4-tetrahydroisoquinoline, m.p. 90°–92°;

(z) 2-(4-phenoxybenzyl)-6-[2-(N-aminocarbonyl-N-hydroxyamino)ethoxy]-1-oxo-1,2,3,4-tetrahydroisoquinoline, m.p. 155°–157°;

(aa) 2-[2-(4-fluorophenoxy)-ethyl]-6-[2-(N-aminocarbonyl-N-hydroxyamino)ethoxy]-1-oxo-1,2,3,4-tetrahydroisoquinoline, m.p. 157°–158°;

(bb) 2-(3-phenylpropyl)-7-[2-(N-aminocarbonyl-N-hydroxyamino)ethoxy]-1-oxo-1,2,3,4-tetrahydroisoquinoline, m.p. 109°–110°, starting from 6-methoxy-1-indanone;

(cc) 2-(3-phenoxybenzyl)-6-[2-(N-aminocarbonyl-N-hydroxyamino)ethoxy]-1-oxo-1,2,3,4-tetrahydroisoquinoline, m.p. 141°–142°;

(dd) 2-[3-(3-pyridyl)propyl]-6-[2-(N-aminocarbonyl-N-hydroxyamino)-ethoxy]-1-oxo-1,2,3,4-tetrahydroisoquinoline, m.p. 146°–147° dec;

(ee) 2-[3-phenyl-2-propen-1-yl]-6-[2-(N-aminocarbonyl-N-hydroxyamino)-ethoxy]-1-oxo-1,2,3,4-tetrahydroisoquinoline, m.p. 133°–134°;

(ff) 2-(2-quinolylmethyl)-6-[2-(N-aminocarbonyl-N-hydroxyamino)-ethoxy]-1-oxo-1,2,3,4-tetrahydroisoquinoline, m.p. 172°–173°; hydrochloride salt, m.p. 189°–191°; hemifumarate salt, m.p. 155°–157°;

(gg) 2-[2-(3-pyridyloxy)-ethyl]-6-[2-(N-aminocarbonyl-N-hydroxyamino)ethoxy]-1-oxo-1,2,3,4-tetrahydroisoquinoline, m.p. 150°–152°;

(hh) 2-[3(4-flurorphenoxy)-benyzl]-6-[2-(N-aminocarbonyl-N-hydroxyamino)-ethoxy]-1-oxo-1,2,3,4-tetrahydroisoquinoline, m.p. 128°–130°;

(ii) 2-[4-(4-fluorophenoxy)-benzyl]-6-[2-(N-aminocarbonyl-N-hydroxyamino)-ethoxy]-1-oxo-1,2,3,4-tetrahydroisoquinoline, m.p. 154°–155°;

(jj) 2-{3-[3-(4-fluorophenoxy)phenyl]propyl}-6-[2-(N-aminocarbonyl-N-hydroxyamino)ethoxy]-1-oxo-1,2,3,4-tetrahydroisoquinole, m.p. 52°–56°;

(kk) 2-{3-[4-(4-fluorophenoxy)phenyl]-6-[2-(N-aminocarbonyl-N-hydroxyamino)-ethoxy]-1-oxo-1,2,3,4-tetrahydroisoquinoline, m.p. 164°–167°;

(ll) 2-(2-naphthylmethyl)-6-[2-(N-aminocarbonyl-N-hydroxyamino)ethoxy]-1-oxo-1,2,3,4-tetrahydroisoquinoline, m.p. 148°–150°;

(mm) 2-(4-biphenylylmethyl)-6-[2-(N-aminocarbonyl-N-hydroxyamino)ethoxy]-1-oxo-1,2,3,4-tetrahydroisoquinoline, m.p. 165°–166°;

(nn) 2-[2-phenylcyclopropylmethyl]-6-[2-(N-aminocarbonyl-N-hydroxyamino)ethoxy]-1-oxo-1,2,3,4-tetrahydroisoquinoline.

EXAMPLE 2

(a) Similarly to procedure described in example 1, 2-(3-phenylpropyl)-6-[3-(N-hydroxyamino)-1-propen-1-yl]-1-oxo-1,2,3,4-tetrahydroisoquinoline is convened to 2-(3-phenylpropyl)-6-[3-(N-aminocarbonyl-N-hydroxyamino)-1-propen-1-yl]-1-oxo-1,2,3,4-tetrahydroisoquinoline, m.p. 131°–133°.

The starting material is prepared as follows:

A solution of m-bromophenethylamine (6.71 g, 33.55 mmol) and Et$_3$N (7 mL, 50.32 mmoL) in CH$_2$Cl$_2$ (100 mL) is cooled to 0° and ethyl chloroformate (4 mL, 50.32 mmoL) is added. After addition is complete the resulting mixture is allowed to come to room temperature and the solvent is removed in vacuo. The residue is then dissolved in EtOAc (200 mL) and the organic phase washed with 2N HCl (1×250 mL), H$_2$O (1×200 mL), saturated NaHCO$_3$ solution (1×200 mL), saturated NaCl solution (1×200 mL), dried over MgSO$_4$ and concentrated in vacuo to give N-ethoxycarbonyl-m-bromophenethylamine.

A suspension of N-ethoxycarbonyl-m-bromophenethylamine (6.87 g, 25.25 mmol) in polyphosphoric acid (50 mL) is heated to reflux for 5 min. When the mixture cools, H$_2$O is added and the resulting solution extracted with EtOAc (1×300 ml). The organic phase is dried and concentrated in vacuo and the residue chromatographed (silica gel, EtOAc) to give 6-bromo-1-oxo-1,2,3,4-tetrahydroisoquinoline.

To a solution of 6-bromo-1-oxo-1,2,3,4-tetrahydroisoquinoline (2.82 g, 12.5 mmol) in DMF (80 ml) is added 1-bromo-3-phenylpropane (2.89 ml, 18.75 mmol), KI (200 mg, 1.25 mmol) and NaH (600 mg, 25 mmol). The reaction mixture is stirred for 3 hours and subsequently poured into H$_2$O (300 ml). The resulting emulsion is extracted with EtOAc (2×150 mL) and the organic phase washed with 2N HCl (1×200 mL), H$_2$O (1×200 mL), saturated NaHCO$_3$ solution (1×200 mL), saturated NaCl solution (2×200 mL), dried over MgSO$_4$ and concentrated in vacuo. The residue is chromatographed (silica gel, 9:1 hexane/EtOAc) to give 2-(3-phenylpropyl)-6-bromo-1-oxo-1,2,3,4-tetrahydroisoquinoline.

To a sealed tube apparatus is added 2-(3-phenylpropyl)-6-bromo-1-oxo-1,2,3,4tetrahydroisoquinoline (1.6 g, 4.65 mmol), CH$_3$CN (8 mL), 1,1-diacetoxy-2-propene (3.4 mL, 23.25 mmol), Pd(OAc)$_2$ (84 mg, 0.37 mmol), P(o-tolyl)$_3$ (113 mg, 0.37 mmol) and Et$_3$N (0.78 mL, 5.58 mmol). The reation vessel is then sealed and the mixture heated to 120° for 48 hours. After cooling to ambient temperature the reaction mixture is diluted with EtOAc (150 mL) and filtered through Celite. The organic phase is washed with saturated NaCl solution (2×200 mL), dried over MgSO$_4$ and concentrated in vacuo. The residue is chromatographed (silica gel, 9:1 hexane/EtOAc, 1:1 hexane/EtOAc, 1:1 hexane/EtOAc) to give 2-(3-phenyl-propyl)-6-(3,3-diacetoxy-1-propen-1-yl)-1-oxo-1,2,3,4-tetrahydroisoquinoline.

2-(3-Phenylpropyl)-6-(3-diacetoxy- 1-propen-1-yl)-1-oxo-1,2,3,4-tetrahydroisoquinoline (330 mg, 79 mmol) is dissolved in tetrahydrofuran (THF, 10 mL) and 6N HCl (20 mL) is added. The resulting solution is stirred for 45 minutes and subsequently neutralized with saturated NaHCO$_3$ solution. The aqueous phase is then extracted with EtOAc (100 ml). The organic phase is dried over MgSO$_4$ and concentrated in vacuo to give 3-[2-(3-phenylpropyl)1-oxo-1,2,3,4-tetrahydroquinolin-6-yl]-acrolein which is used without further purification and convened according to procedures described in example 1 to the oxime and subsequently to 2-(3-phenylpropyl)-6-[3-(N-hydroxyamino)-1-propen-1-yl]-1-oxo-1,2,3,4-tetrahydroisoquinoline.

Similarly prepared is:
(b) 2-Benzyl-6-[3-(N-aminocarbonyl-N-hydroxyamino)-1-propen-1-yl]-1-oxo-1,2,3,4-tetrahydroisoquinoline.
(c) 2-[3-(4-fluorophenyl)propyl]-6-[3-(N-aminocarbonyl-N-hydroxyamino)-1-propen-1-yl]-1-oxo-1,2,3,4-tetrahydroisoquinoline.

EXAMPLE 3

(a) Similarly to procedure described in Example 1, 2-(3-phenylpropyl)-6-[2-(N-hydroxyamino)-propyloxy]-1-oxo-1,2,3,4-tetrahydroisoquinoline is converted to 2-(3-phenylpropyl)-6-[2-(N-aminocarbonyl-N-hydroxyamino)-propyloxy]-1-oxo-1,2,3,4-tetrahydroisoquinoline, m.p. 170°–172°.

The starting material is prepared as follows:
6-Methoxy-1-oxo-1,2,3,4-tetrahydroisoquinoline (example 1) is condensed with 1-bromo-3-phenylpropane under N-alkylation conditions described in example 1 to yield 6-methoxy-2-(3-phenylpropyl)-1-oxo-1,2,3,4-tetrahydroisoquinoline.

Treatment with BBr$_3$ under conditions described in Example 1 yields 6-hydroxy-2-(3-phenylpropyl)-1-oxo-1,2,3,4-tetrahydroisoquinoline.

To a solution of 6-hydroxy-2-(3-phenylpropyl)-1-oxo-1,2,3,4-tetrahydroisoquinoline (1.5 g, 5.34 mmol) in acetone (80 ml) is added 3-chloro-2-methylpropene (8 ml, 8.01 mmol), Cs$_2$CO$_3$ and a catalytic amount of KI. The reaction is then refluxed for 24 hours. After this time the reaction mixture is cooled to ambient temperature and filtered. The filter cake is washed with acetone (3×50 ml) and the combined organics concentrated in vacuo. The residue is chromatographed (silica gel, 1:4 EtOAc/hexane) to give 6-(2-methyl-2-propenyloxy)-2-(3-phenylpropyl)-1-oxo-1,2,3,4-tetrahydroisoquinoline.

Treatment of 6-(2-methyl-2-propenyloxy)-2-(3-phenylpropyl)-1-oxo-1,2,3,4-tetrahydroisoquinoline with ozone under conditions of ozonolysis described in example 1 yields 6-(2-oxopropyloxy)-2-(3-phenylpropyl)-1-oxo-1,2,3,4-tetrahydroisoquinoline.

Conversion to the oxime and reduction thereof according to procedures described in Example 1 yields 2-(3-phenylpropyl)-6-[2-(N-hydroxyamino)-propyloxy]-1-oxo-1,2,3,4tetrahydroisoquinolin

EXAMPLE 4

(a) Similarly to procedures described in Example 1, 2-benzyl-6-[3-(N-hydroxyamino)-1-propen-1-yl]-1-oxo-1,2-dihydroisoquinoline is converted to 2-benzyl-6-[3-(N-aminocarbonyl-N-hydroxyamino)-1-propen-1-yl]-1-oxo-1,2-dihydroisoquinoline, m.p. 172°–174°.

The starting material is prepared as follows:
To a 0° solution of 3'-bromocinnamic acid (5 g, 22 mmol) in CH$_2$Cl$_2$ (50 mL) is added oxalyl chloride (2.9 mL, 38 mmol) and a single drop of dimethylformamide (DMF). The reaction is allowed to come to ambient temperature and is concentrated in vacuo, when gas ceases to evolve. The residue is redissolved in dioxane ( 10 mL) and the resulting mixture is cooled to 0°. A solution of NaN$_3$ (4.29 g, 66 mmol) in dioxane/H$_2$O ( 1:1, 25 mL) is then added and the reaction allowed to come to ambient temperature. The resulting solution is diluted with H$_2$O (100 mL) and the aqueous phase extracted with Et$_2$O (2×100 mL). The combined organics are washed with saturated NaHCO$_3$ solution (1×250 mL), saturated NaCl solution (1×250 mL), dried over MgSO$_4$ and concentrated in vacuo to give 3'-bromocinnamoyl azide.

The acyl azide (5.42 g, 21.5 mmol) and several crystals of iodine are dissolved in 1,2-dichlorobenzene (20 mL) and the resulting mixture heated to reflux for 24 hours. After this time the solution is cooled to 0° and a precipitate forms. This material is collected and washed with hexanes (3×50 mL) to afford 6-bromo-1,2-dihydro-1-oxoisoquinoline.

Treatment with benzyl bromide and NaH in DMF, water conditions previously described in example 2, yields after chromatography (silica gel, 1:4, EtOAc/hexane) 2-benzyl-6-bromo-1,2-dihydro-1-oxoisoquinoline.

A mixture of 2-benzyl-6-bromo-1,2-dihydro-1-oxoisoquinoline (1 g, 3.2 mmol), acrolein dimethyl acetal (2.6 mL, 22.4 mmol), Pd(OAc)$_2$ (15 mg, 0.064 mmol), P(o-tolyl)$_3$ (78 mg, 0.26 mmol) and Et$_3$N (0.5 mL, 3.84 mmol) in DMF (2 mL) is heated in a sealed tube apparatus at 120° for 48 hours. After cooling to room temperature, the reaction mixture is diluted with EtOAc, filtered, washed with saturated NaCl solution, dried over MgSO$_4$ concentrated in vacuo, and the residue is chromatographed (silica gel 1:4 EtOAc/hexane) to yield 3-[2-benzyl-1-oxo-1,2-dihydroisoquinolin-6-yl ]-acrolein.

Using a sequence of reactions similarly to sequence described in example 2, the aldehyde is converted to 2-benzyl-6-[3-(N-hydroxyamino)-1-propen-1-yl]-1-oxo-1,2-dihydroisoquinoline.

(b) Similarly prepared is 2-(3-phenylpropyl)-6-[3-(N-aminocarbonyl-N-hydroxyamino)-1-propen-1-yl]-1-oxo-1,2-dihydroisoquinoline.

(c) Similarly prepared is 2-(3-phenylpropyl)-6-[3-(N-aminocarbonyl-N-hydroxyamino)-1-propen-1- yl]3,4-dihydro-2H-1,2-benzothiazine-1,1-dioxide. The starting 6-bromo-2-(3-phenylpropyl)-3,4-dihydro-2H-1,2-benzothiazine-1,1-dioxide is prepared similarly to 6-methoxy-2-(3-phenylpropyl)-3,4-dihydro-2H-1,2-benzothiazine-1,1-dioxide described in example 10.

EXAMPLE 5

Similarly to procedure described in Example 1, 2-(3-phenylpropyl)-6-[3-(N-hydroxyamino)-propyloxy]-1-oxo-1,2,3,4-tetrahydroisoquinoline is convened to 2-(3-phenylpropyl)-6-[3-(N-aminocarbonyl-N-hydroxyamino)-propyloxy]-1-oxo-1,2,3,4-tetrahydroisoquinoline, m.p. 106°–109°.

The starting material is prepared as follows:

A solution of 6-hydroxy-2-(3-phenylpropyl)-1-oxo-1,2,3,4-tetrahydroisoquinoline (7.55 g, 26.87 mmol), $Cs_2CO_3$ (18 g, 53.74 mmol) and chloropropionaldehyde diethyl acetal (5.4 mL, 32.2 mmol) in DMF (100 mL) is stirred for 48 hours. After this time the reaction is diluted with $H_2O$ (400 mL) and the resulting mixture extracted with EtOAc (2×200 mL). The combined organic phases are washed with saturated NaCl solution (2×400 mL), dried over $MgSO_4$ and concentrated in vacuo. The residue is chromatographed (silica gel, 1:9 EtOAc/hexane) to give 2-(3-phenylpropyl)-6-(3,3-diethoxypropyloxy)-1-oxo-1,2,3,4-tetrahydroisoquinoline which is hydrolyzed with 6N HCl in tetrahydrofuran at room temperature to yield β-[2-(3-phenylpropyl)-1-oxo-1,2,3,4-tetrahydroisoquinolin-6-yloxy]-propionaldehyde.

Conversion to the oxime and reduction thereof according to procedures described in example 1 yields 2-(3-phenylpropyl)-6-[3-N-hydroxyamino)-propyloxy]-1-oxo-1,2,3,4-tetrahydroisoquinoline.

Similarly prepared are:
(b) 2-benzyl-6-[3-(N-aminocarbonyl-N-hydroxyamino)-propyloxy]-1-oxo-1,2-dihydroisoquinoline, m.p. 149°–150°, starting with 2-benzyl-6-methoxy-1,2-dihydro-1-oxoisoquinoline (prepared according to example 4).
(c) 2-(3-phenylpropyl)-7-[3-(N-aminocarbonyl-N-hydroxyamino)-propyloxy]-1-oxo-1,2,3,4-tetrahydroisoquinoline, m.p. 98°–100°, starting from 7-hydroxy-2-(3-phenylpropyl)-1-oxo-1,2,3,4-tetrahydroisoquinoline, prepared according to procedures in prior examples from 7-methoxy-1-oxo-1,2,3,4-tetrahydroisoquinoline (which is in turn prepared from 6-methoxy-1-indanone).
(d) 2-(3-phenylpropyl)-6-[3-[N-aminocarbonyl-N-hydroxyamino)-propyloxy]-3,4-dihydro-2H-1,2-benzothiazine-1,1-dioxide prepared from 6-hydroxy-2-(3-phenylpropyl)-3,4-dihydro-2H-1,2-benzothiazine-1,1-dioxide (example 10).
(e) 2-(2-pyridylmethyl)-6-[2-(N-aminocarbonyl-N-hydroxyamino)-ethoxy]-1-oxo-1,2,3,4-tetrahydroisoquinoline, m.p. 158°–160°.

The starting material is prepared as follows using methodology similar to that described in the previously examples.

6-Hydroxy-1-oxo-1,2,3,4-tetrahydroisoquinoline is treated with bromoacetaldehyde dimethyl acetal, in the presence of $Cs_2CO_3$ and CsI in DMF to yield 6-(2,2-dimethoxyethoxy)-1-oxo-1,2,3,4-tetrahydroisoquinoline. Treatment with 2-chloromethylpyridine hydrochloride in the presence of sodium hydride in DMF yields 6-(2,2-dimethoxyethoxy) 2-(2-pyridylmethyl)-1-oxo-1,2,3,4-tetrahydroisoquinoline. Hydrolysis with 20% aqueous sulfuric acid in THF yields α-[2-(2-pyridylmethyl)-1-oxo-1,2,3,4-tetrahydroisoquinolin-6-yloxy]-acetaldehyde which is then converted to 2-(2-pyridylmethyl)-6-[2-(N-hydroxyamino)-ethoxy]-1-oxo-1,2,3,4-tetrahydroisoquinoline.

(f) 2-[3-(2-thienyl)-propyl]-6-[2-(N-aminocarbonyl-N-hydroxyamino)-ethoxy]-1-oxo-1,2,3,4-tetrahydroisoquinoline, m.p. 124°–127°;

EXAMPLE 6

(a) 2-(3-Phenylpropyl)-6-[2-(N-hydroxyamino)-ethoxy]-1-oxo-1,2,3,4-tetrahydroisoquinoline (498 mg, 1.5 mmol) is dissolved in dioxane t 15 mL) and methyl isocyanate (0.22 mL, 3.7 mmol) is added. After 12 hours, the reaction mixture is diluted with EtOAc (150 mL) and the organic phase washed with 2N HCl (2×200 mL), $H_2O$ (4×200 mL), saturated $NaHCO_3$ solution (2×200 mL), saturated NaCl solution (2×200 mL), dried over $MgSO_4$ and concentrated in vacuo. The resulting material is triturated with hexanes and recrystallized from $CH_2C_2$/hexanes to give 2-(3-phenylpropyl)-6-{2-[N-(methylaminocarbonyl)-N-hydroxyamino]-ethoxy}-1-oxo-1,2,3,4-tetrahydroisoquinoline, m.p. 138°–139°.

Similarly prepared are:
(b) 2-benzyl-6-{2-[N-(methylaminocarbonyl)-N-hydroxyamino]-ethoxy}-1-oxo-1,2,3,4-tetrahydroisoquinoline;
(c) 2-benzyl-6-{2-[N-(3,4,5-trimethoxyanilinocarbonyl)-N-hydroxyamino]-ethoxy}-1-oxo-1,2,3,4-tetrahydroisoquinoline, m.p. 155°–156°;
(d) 2-(3-phenylpropyl)-6-{2-[N-(3,4,5-trimethoxyanilinocarbonyl)-N-hydroxyamino]-ethoxy}-1-oxo-1,2,3,4-tetrahydroisoquinoline, m.p. 89°–90°;
(e) 2-(3-phenylpropyl)-6-{3-[N-(methylaminocarbonyl)-N-hydroxyamino]-1-propen-1-yl}-1-oxo-1,2,3,4-tetrahydroisoquinoline;
(f) 2-(3-phenylpropyl)-6-{3-[N-(ethylaminocarbonyl)-N-hydroxyamino]-propyloxy}-1-oxo-1,2,3,4-tetrahydroisoquinoline;
(g) 2-(3-phenylpropyl)-6-{2-[N-(methylaminocarbonyl)-N-hydroxyamino]-ethoxy}-1-oxo-1,2-dihydroisoquinoline;
(h) 2-(3-phenylpropyl)-6-{3-[N-(methylaminocarbonyl)-N-hydroxyamino]-propyloxy}-3,4-dihydro-2H-1,2-benzothiazine-1,1-dioxide prepared from 6-hydroxy-2-(3-phenylpropyl)-3,4-dihydro-2H-1,2-benzothiazine-1,1-dioxide (example 10).
(i) 2-[3-(4-fluorophenyl)propyl)-6-{2-[-N-methylaminocarbonyl)-N-hydroxyamino]-ethoxy}-3,4-dihydro-2H-1,2-benzothiazine-1,1-dioxide prepared from 6-hydroxy-2-(3-phenylpropyl)-3,4-dihydro-2H-1,2-benzothiazine-1-dioxide (example 10).

EXAMPLE 7

(a) A solution of 2-[3-(4-fluorophenyl)-propyl]-6-[2-(N-aminocarbonyl-N-hydroxyamino)-ethoxy]-1-oxo-1,2,3,4-tetrahydroisoquinoline (500 mg, 1.2 mmol) and triethylamine (0.2 mL, 1.4 mmol) are dissolved in THF (25 mL) and acetyl chloride (0.1 mL, 1.4 mmol) is added. The reaction mixture is stirred for 2 hours and subsequently poured into 2N HCl. The aqueous phase is extracted with EtOAc (3×100 mL) and the combined organics washed with 2N HCl (2×100 mL) $H_2O$ (2×100 mL), saturated $NaHCO_3$ solution (2×100 mL), saturated NaCl solution (2×100 mL), dried over $MgSO_4$ and concentrated in vacuo. The residue is triturated with hexanes and chromatographed (silica gel, 1:1 EtOAc/hexane). The resulting material is crystallized from cold $CH_2Cl_2/Et_2O$ and dried in vacuo to give 2-[3-(4-fluorophenyl)-propyl]-6-{2-[N-(aminocarbonyl)-N-(acetyloxy)amino]-ethoxy}-1-oxo-1,2,3,4-tetrahydroisoquinoline, m.p. 113°–114°.

(b) Similarly prepared is 2-(4-fluorobenzyl)-6-{2-[N-(aminocarbonyl)-N-(acetyloxy)amino]-ethoxy}-1-oxo-1,2,3,4-tetrahydroisoquinoline, m.p. 160°–162°.

(c) Similarly prepared is 2-(4-fluorobenzyl)-6-{2-[N-(aminocarbonyl)-N-(3-methoxycarbonylpropionyloxy)-amino]ethoxy}-1-oxo-1,2,3,4-tetrahydroisoquinoline, m.p. 109°–110°.

(d) Similarly prepared is 2-[3-(4-fluorophenyl)-propyl-6-{2-[N-(aminocarbonyl)-N-(3-methoxycarbonylpropionyloxy)-amino]ethoxy}-1-oxo-1,2,3,4-tetrahydroisoquinoline, m.p. 55°–57°.

EXAMPLE 8

A solution of 2-[3-(4-fluorophenyl)-propyl]-6-[2-(N-hydroxyamino)-ethoxy]-1-oxo-1,2,3,4-tetrahydroisoquinoline (900 mg) in 25 ml of tetrahydrofuran is cooled to 0°. Acetyl chloride (0.50 g) is slowly added and the mixture is stirred for one hour at 0°. The mixture is then diluted with ethyl acetate and washed with aqueous 2N HCl, dried ($MgSO_4$) and evaporated to give 2-[3-(4-fluorophenyl)-propyl]-6-[2-(N-acetyloxy-N-acetylamino)ethoxy]-1-oxo-1,2,3,4-tetrahydroisoquinoline.

EXAMPLE 9

2-[3-(4-Fluorophenyl)-propyl]-6-2-(N-acetyloxy-N-acetylamino)-ethoxy]-1-oxo-1,2,3,4-tetrahydroisoquinoline (2.0 g) is dissolved in 40 ml of an isopropanol/water mixture (1:1) and treated with 0.94 g (25 mmol) of lithium hydroxide monohydrate for 30 minutes at room temperature. The mixture is diluted with ether and the organic phase is removed. The aqueous layer is brought to pH of approximately 3 with 2N HCl, and extracted with ether. The combined acidic extracts are dried ($MgSO_4$) and evaporated to dryness to yield 2-[3-(4-fluorophenyl)-propyl]-6-[2-(N-hydroxy-N-acetylamino)-ethoxy]-1-oxo-1,2,3,4-tetrahydroisoquinoline.

EXAMPLE 10

(a) Similarly to procedure described in example 1, 2-(3-phenylpropyl)-6-[2-(N-hydroxyamino)-ethoxy]-3,4-dihydro-2H-1,2-benzothiazine-1,1-dioxide is reacted with trimethylsilyl isocyanate to yield 2-(3-phenylpropyl)-6-[2-(N-aminocarbonyl-N-hydroxyamino)-ethoxy]-3,4-dihydro-2H-1,2-benzothiazine-1,1-dioxide, m.p. 134°–135°.

The starting material is prepared as follows:

Ethyl 3-methoxyphenylacetate (20 g, 103 mmol) is added at 0° to a solution of chlorosulfonic acid (34.2 mL, 515 mmol). After 1 hour, the reaction is cautiously poured onto ice and $H_2SO_4$ (100 mL) is added. The resulting emulsion is extracted with EtOAc (1×250 mL). The organic phase is washed with $H_2O$ (2×200 mL), dried over $MgSO_4$ and concentrated in vacuo. The crude residue is dissolved in $Et_2O$ (200 mL) and carefully added at 0° to a solution of 3-phenyl-1-propylamine (15.3 g, 113 mmol) and $Et_3N$ (20 mL, 144 mmol) in $Et_2O$ (100 mL). After ½ hour the reaction mixture is poured into 2N HCl (200 mL) and the organic phase washed with 2N HCl (1×200 mL), $H_2O$ (2×200 mL), saturated $NaHCO_3$ solution (2×200 mL), saturated NaCl solution (2×200 mL), dried over $MgSO_4$ and concentrated in vacuo to give ethyl 2-[N-3-phenylpropylamino)-sulfonyl]-3-methoxyphenylacetate.

Sodium Methoxide (280 mg, 5.1 mmol) and ethyl 2-[(N-3-phenylpropylamino)-sulfonyl]-3-methoxyphenylacetate (2.0 g, 5.1 mmol) are dissolved in toluene (200 mL) and the resulting solution is refluxed for 24 hours. An additional portion of sodium methoxide (60 mg, 1.1 mmol) is added and the reaction is once again refluxed for 24 hours. The reaction mixture is subsequently diluted with EtOAc (200 mL) and $H_2O$ (200 mL). The organic phase is then washed with saturated NaCl solution (2×200 mL), dried over $MgSO_4$ and concentrated in vacuo to give 6-methoxy-2-(3-phenylpropyl)-3-oxo-3,4-dihydro-2H-1,2-benzothiazine-1,1-dioxide.

To a 1M $BH_3$ solution (300 mL, 30 mmol) @ 0° is added a solution of 6-methoxy-2-(3-phenylpropyl)-3-oxo-3,4-dihydro-2H-1,2-benzothiazine-1,1-dioxide (3.3 g, 9.6 mmol) in anhydrous THF (75 mL). After addition is complete the reaction mixture is brought to reflux for 2 hours. When the mixture has cooled to ambient temperature 6N HCl is carefully added until gas evolution ceases. The volatiles are removed in vacuo and the residue extracted with EtOAc (200 mL). The organic phase is washed with saturated NaCl solution (2×200 mL), dried over $MgSO_4$ and concentrated in vacuo. The resulting material is chromatographed (silica gel, 1:2 EtOAc/hexanes) to afford 6-methoxy-2-(3-phenylpropyl)-3,4-dihydro-2H-1,2-benzothiazine-1,1-dioxide.

6-Methoxy-2-(3-phenylpropyl)-3,4-dihydro-2H-1,2-benzothiazine-1,1-dioxide (1.2 g, 4 mmol) is dissolved in $CH_2Cl_2$ (200 mL) and the resulting solution is cooled to −78°. Boron tribromide (1.1 mL, 12 mmol) is then added and the reaction is allowed to come to ambient temperature. After 12 hours the mixture is cooled to 0° and subsequently neutralized with saturated $NaHCO_3$ solution (100 mL). The aqueous phase is then extracted with $CH_2Cl_2$ (1×100 mL). The combined organics are washed with saturated NaCl solution (2×200 mL), dried over $Na_2SO_4$ and concentrated in vacuo to give 6-hydroxy-2-(3-phenylpropyl)-3,4-dihydro-2H-1,2-benzothiazine-1,1-dioxide.

Similarly to procedures described in example 1, 6-hydroxy-2-(3-phenylpropyl)-3,4-dihydro-2H-1,2-benzothiazine-1,1-dioxide is converted to 2-(3-phenylpropyl)-6-[2-(N-hydroxyamino)ethoxy]-3,4-dihydro-2H-1,2-benzothiazine-1,1-dioxide.

EXAMPLE 11

Similarly to the procedures described herein are prepared:

(a) 2-(3-phenylpropyl)-7-[2-(N-aminocarbonyl-N-hydroxyamino)ethoxy]-1-oxo-2,3,4,5-tetrahydro-2(1H)-benzazepine starting from 7-hydroxy-2-(3-phenylpropyl)-1-oxo-2,3,4,5-tetrahydro-2(1H)-benzazepine which can in turn be prepared from 6-methoxytetralone;

(b) 2-(3-phenylpropyl)-5-[2-(N-aminocarbonyl-N-hydroxyamino)ethoxy]-1-oxo-1,3-dihydro-3H-benzo[c]pyrrole m.p. 159°–160°, starting from 5-hydroxy-2-(3-phenylpropyl)-1-oxo-1,3-dihydrobenzo[c]pyrrole.

The starting material is prepared as follows:

To a solution of p-methoxybenzoyl chloride (37.8 g, .222 mol) in $CH_2Cl_2$ (200 ml) at 0°, is added triethylamine (22.5 g, .222 mol) followed by the slow addition of 3-phenylpropylamine (20 g,.148 mol) dissolved in CH$_2$Cl$_2$ (100 ml). The reaction is allowed to warm to room temperature over several hours. The solvent is removed in vacuo, and the residue is dissolved in EtOAc (500 ml) and 2N HCl (500 ml). The EtOAc is separated, washed with 2NHCl (350 ml), H$_2$O (350 ml), saturated NaHCO$_3$ solution (350 ml), and saturated NaCl solution (350 ml); dried over MgSO$_4$; and evaporated. The resulting light brown solid is purified by chromatography (SiO$_2$;1:9 EtOAc/hexanes, 1:4 EtOAc/hexanes) yielding N-(3-phenylpropyl)-4-methoxybenzamide as creamy solid.

A solution of N-(3-phenylpropyl)-4-methoxybenzamide (5 g, 18.58 mmol) in dry THF (100 ml) is chilled to 5° in an ice/H$_2$O bath. To this, n-butyllithium (1.6 m in hexanes, 59.46 mmol, 37 ml) is added slowly so that the temperature remains below 15°. After the addition is complete, the reaction is stirred for 5 minutes at 5°, followed by the addition of dimethylformamide (4.5 g, 61.31 mmol). After stirring for 1 hour at 10°, saturated NH$_4$Cl solution (10 ml) is added, and the reaction is allowed to warm to room temperature. The reaction is poured into saturated NaCl solution (300 ml) and extracted into EtOAc (300 ml). The EtOAc phase is washed with 2N HCl (300 ml), H$_2$O (300 ml) and saturated NaCl solution (300 ml) dried over MgSO$_4$ and evaporated. The product is purified by chromatography (SiO$_2$; 1:9 EtOAc/hexanes, 1:4 EtOAc/hexanes, 2:3 EtOAc/hexanes) yielding 2-(3-phenylpropyl)-5-methoxy-3-hydroxy-1-oxo-1,3-dihydrobenzo[c]pyrrole, as a white solid.

2-(3-Phenylpropyl)-5-methoxy-3-hydroxy-1-oxo- 1,3-dihydrobenzo[c]pyrrole (2.49 g, 8.38 mmol) is dissolved in HCl/EtOH (50 ml concentrated HCl, 150 ml EtOH), and N$_2$ is bubbled through the solution for 10 minutes followed by the addition of the catalyst, 10% Pd/C (200 mg). The mixture is hydrogenated on a Parr-Shaker apparatus at 3 atmospheres pressure for 3 hours. After filtering the reaction through a pad of Celite, the filtrate is concentrated in vacuo, and the residue is dissolved in EtOAc (200 ml). The EtOAc is washed with 2N HCl (200 ml), H$_2$O (200 ml), saturated NaHCO$_3$ solution (200 ml) and saturated NaCl solution (200 ml) dried over MgSO$_4$ and evaporated. The product is purified by chromatography (SiO$_2$; 1:9 EtOAc/hexanes, 1:4 EtOAc/hexanes) to yield 2-(3-phenylpropyl)-5-methoxy-1-oxo-1,3-dihydrobenzo[c]pyrrole. Treatment with BBr$_3$ yields 2-(3-phenylpropyl)-5-hydroxy-1-oxo-1,3-dihydrobenzo[c]pyrrole.

EXAMPLE 12

To a solution of 2-(4'-fluoro-4-biphenylylmethyl)-6-[2-(N-hydroxyamino)ethoxy]-1-oxo-1,2,3,4-tetrahydroisoquinoline (~22.5 mmol) in 1,4-dioxane (50 ml) and methylene chloride (30 ml), is added trimethylsilylisocyanate (3.36 ml). The reaction mixture is stirred at room temperature overnight and is subsequently diluted with H$_2$O (500 ml). The resulting solution is extracted with EtOAc (2×400 ml) and the combined EtOAc portions washed with 2N HCl (800 ml), saturated NaCl solution (800 ml), dried over MgSO$_4$, and concentrated in vacuo. The resulting solid is recrystallized from EtOAc/hexanes to give 2-(4'-fluoro-4-biphenylylmethyl)-6-[2-(N-aminocarbonyl-N-hydroxyamino)-ethoxy]-1-oxo-1,2,3,4-tetrahydroisoquinoline, m.p. 171°-172°.

The starting material is prepared as follows:

A solution of 1,1'-bis(diphenylphosphine)-ferrocene (1.69 g, 3.05 mmol) and palladium acetate (515 mg, 2.29 mmol) in DMF (250 ml), is heated at 50° for 10 minutes. After the solution has cooled to room temperature methyl p-iodobenzoate (20 g, 76 mmol), 4-fluorobenzenboronic acid (20 g, 143 mmol) and K$_2$CO$_3$ (15.8 g, 114 mmol) are added. The resulting mixture is then heated to 90° for 24 hours. After once again cooling to room temperature the reaction mixture is filtered through Celite and the filtrate washed with EtOAc (3×100 ml). The combined organic portions are then washed with 2N HCl (100 ml), saturated NaCl solution (100 ml), 1N NaOH (100 ml), dried over MgSO$_4$, and concentrated in vacuo. The resulting brown solid is chromatographed (silica gel; hexanes, 1% EtOAc/hexanes) to afford methyl 4'-fluoro-4-biphenylyl-carboxylate as a white solid.

To a suspension of lithium aluminum hydride (2.86 g, 74.4 mmol) in THF (300 ml) at 0°, is added methyl 4'-fluoro-4-biphenylyl-carboxylate (8.67 g. 37.7 mmol) as a solution in THF (100 ml). The resulting mixture is stirred for 1 hour and subsequently allowed to warm to room temperature. The reaction mixture is chilled to 0° and 2N HCl (100 ml) is slowly added. The resulting mixture then is extracted with Et$_2$O (2×150 ml). The combined organic portions are washed with saturated NaHCO$_3$ solution (400 ml), saturated NaCl solution (400 ml), dried over MgSO$_4$ and concentrated in vacuo to yield 4'-fluoro-4-biphenylyl-methanol as a white solid.

To a solution of 4'-fluoro-4-biphenylylmethanol (7.38 g, 36.93 mmol) in Et$_2$O (250 ml) is added phosphorous tribromide (7 ml, 73.06 mmol). The reaction is allowed to warm slowly to room temperature and is then refluxed for 12 hours. After the reaction is cooled to room temperature ice chips are added until gas no longer evolves. The reaction mixture is then diluted with H$_2$O (200 ml) and extracted with 1N NaOH (300 ml) and saturated NaCl solution (300 ml), dried over MgSO$_4$, and concentrated in vacuo to give 4'-fluoro-4-biphenylylmethyl bromide as a white solid.

6-Hydroxy-1-oxo-1,2,3,4-tetrahydroisoquinoline can be prepared as described in example 1 or as follows:

Hydroxylamine hydrochloride (8.57 g, 123 mmol) is added all at once to a stirred room temperature solution of 5-methoxy-1-indanone (10 g, 61.7 mmol) and potassium carbonate (9.37 g, 67.82 mmol, powdered) in methanol (153 ml) and water (12 ml). The mixture is heated at reflux for 3 hours and then stirred overnight at room temperature. The solution is then poured into ice water (600 ml). The resulting tan precipitate is collected by vacuum filtration and air dried, to yield the oxime, m.p. 156°-158°.

Phosphorous pentoxide (1.0 g, 7.1 mmol) is added all at once to methanesulfonic acid (10 g, 104.1 mmol) and stirred for 3 hours at room temperature. 5-Methoxy-1-indanone oxime (100 mg, 0.53 mmol) is added in portions, with each portion allowed to dissolve completely before the next is added. The stirred reaction mixture is heated at 100° for 1.5 hours. The reaction is quenched by the addition of saturated sodium bicarbonate (10 ml) and extracted with 3×5 ml dichloromethane. The combined organic layers are dried over magnesium sulfate and concentrated in vacuo to yield the 6-methoxy-1-oxo-1,2,3,4-tetrahydroisoquinoline. Treatment with boron tribromide (see example 1 ) yields 6-hydroxy-1-oxo-1,2,3,4-tetrahydroisoquinoline.

To a solution of 6-hydroxy-1-oxo-1,2,3,4-tetrahydroisoquinoline (25 g, 15.3 mmol), CsI (4 g, 15.3 mmol) and bromoacetaldehyde dimethyl acetal (40 ml, 338 mmol) in DMF (600 ml) is added Cs$_2$CO$_3$ (137.5 g, 460 mmol). The reaction mixture is heated at 60° overnight. After this time, the reaction is poured into 1 liter brine and the resulting suspension is extracted with EtOAc (4×400 ml). The combined EtOAc extracts are dried over MgSO$_4$ and concentrated in vacuo. The residue is washed with Et$_2$O to yield 6-(2,2-dimethoxyethoxy)-1-oxo-1,2,3,4-tetrahydroisoquinoline as a crystalline solid.

To a solution of 6-(2,2-dimethoxyethoxy)-1-oxo-1,2,3,4-tetrahydroisoquinoline (5.79 g, 23.05 mmol) and 4'-fluoro-4-biphenylylmethyl bromide (9.16 g, 34.57 mmol), in DMF (100 ml) is added sodium hydride (1.1 g, 27.5 mmol) and a catalytic amount of potassium iodide. The reaction mixture is stirred for 2 hours at room temperature and is subsequently diluted with H$_2$O (500 ml). The mixture is then extracted with EtOAc (2×300 ml). The combined EtOAc portions are washed with saturated NaCl solution (600 ml), dried over MgSO$_4$, and concentrated in vacuo and washed with hexanes to yield the acetal, 2-(4'-fluoro-4-biphenylylmethyl)-6-(2,2-dimethoxyethoxy)-1-oxo-1,2,3,4-tetrahydroisoquinoline.

To a solution of the above acetal (~23 mmol) in THF (100 ml) is added 6N HCl (200 ml). The reaction mixture is heated to reflux and immediately allowed to cool to room temperature. The resulting mixture is diluted with H$_2$O (400 ml) and extracted with EtOAc (2×250 ml). The combined EtOAc portions are washed with saturated NaHCO$_3$ solution (500 ml), saturated NaCl solution (500 ml), dried over MgSO$_4$, and concentrated in vacuo to yield α-[2-(4'-fluoro-4-biphenylylmethyl)-1,2,3,4-tetrahydroisoquinolin-6-yloxy]-acetaldehyde.

To a solution of the above aldehyde (~23 mmol) in pyridine (20 ml) and EtOH (20 ml) is added hydroxylamine hydrochloride (3.2 g, 46 mmol). The reaction mixture is stirred overnight. The solvent is removed in vacuo and the residue dissolved in EtOAc (300 ml) and 2N HCl (300 ml). The EtOAc portion is washed with saturated NaHCO$_3$ solution (300 ml), saturated NaCl solution (300 ml), dried over MgSO$_4$, and concentrated in vacuo. The resulting material is purified by chromatography (silica gel 1:9 EtOAc/hexanes, 1:4 EtOAc/hexanes and 2:3 EtOAc/hexanes) yielding α-[2-(4'-fluoro-4-biphenylylmethyl)-1-oxo-1,2,3,4-tetrahydroisoquinolin-6-yloxy]-acetaldehyde oxime.

To a solution of the above oxime (9 g, 22.28 mmol) in glacial acetic acid (50 ml) and CH$_2$Cl$_2$ (75 ml) is added sodium cyanoborohydride (1.7 g). The solution is stirred for 45 minutes at room temperature and subsequently diluted with H$_2$O (200 ml). The resulting mixture is then neutralized with 5N NaOH and solid NaHCO$_3$. The reaction mixture is extracted with EtOAc (2×200 ml) and the combined organic layers washed with saturated NaCl solution, dried over MgSO$_4$, and concentrated in vacuo to yield 2-(4'-fluoro-4-biphenylylmethyl)-6-[2-(N-hydroxyamino)ethoxyl]-1-oxo-1,2,3,4-tetrahydroisoquinoline.

EXAMPLE 13

Similarly to procedures described in the previous examples are prepared:

(a) 2-[trans-2-phenylcyclopropylmethyl]-6-[2-(N-aminocarbonyl-N-hydroxyamino)ethoxy]-1-oxo-1,2,3,4-tetrahydroisoquinoline, m.p. 122°–125°;

(b) 2-(1-naphthylmethyl)-6-[2-(N-aminocarbonyl-N-hydroxyamino)ethoxy]-1-oxo-1,2,3,4-tetrahydroisoquinolin m.p. 153°–155°;

(c) 2-(2-naphthyloxyethyl)-6-[2-(N-aminocarbonyl-N-hydroxyamino)ethoxy]-1-oxo-1,2,3,4-tetrahydroisoquinoline, m.p. 144°–146°;

(d) 2-(2-thienylmethyl)-6-[2-(N-aminocarbonyl-N-hydroxyamino)ethoxy]-1-oxo-1,2,3,4-tetrahydroisoquinoline, m.p. 147°–149°;

(e) 2-[3-(4-fluorophenyl)-2-propen-1-yl]-6-[2-(N-aminocarbonyl-N-hydroxyamino)ethoxy]-1-oxo-1,2,3,4-tetrahydroisoquinoline, m.p. 129°–130°;

(f) 2-[3-(2,4-difluorophenyl)-2-propen-1-yl]-6-[2-(N-aminocarbonyl-N-hydroxyamino)ethoxy]-1-oxo-1,2,3,4-tetrahydroisoquinoline, m.p. 100°–101°;

(g) 2-[3-chromenylmethyl]-6-[2-(N-aminocarbonyl-N-hydroxyamino)ethoxy]-1-oxo-1,2,3,4-tetrahydroisoqui e, m.p. 135°–138°;

(h) 2-[2-biphenylylmethyl]-6-[2-(N-aminocarbonyl-N-hydroxyamino)ethoxy]-1-oxo-1,2,3,4-tetrahydrois m.p. 135°–137°;

(i) 2-(4-biphenylyl)-6-[2-(N-aminocarbonyl-N-hydroxyamino)ethoxy]-1-oxo-1,2,3,4-tetrahydroisoquinoline, m.p. 185°–187°; and (j) 2-(3-biphenyl)-6-[2-(N-aminocarbonyl-N-hydroxyamino)-ethoxy]-1-oxo-1,2,3,4-tetrahydroisoquinoline, m.p. 143°–145°.

The intermediate, 6-(2,2-dimethoxyethoxy)-2-(3-biphenylyl)-1-oxo-1,2,3,4-tetrahydroisoquinolin is prepared as follows:

To a solution of 6-(2,2-dimethoxyethoxy)-1-oxo-1,2,3,4-tetrahydroisoquinoline (1.5 g, 5.98 mmol) and 3-bromobiphenyl (2.79 g, 11.96 mmol) in DMF (60 ml) is added NaH (215 mg, 8.97 mmol) and CuI (114 mg, .6 mmol). The reaction is refluxed overnight. After allowing the reaction to cool to room temperature, it is diluted with water (300 ml). The product is extracted into EtOAc (2×150 ml), and the organic layer is washed with 1N NaOH (300 ml) and saturated sodium chloride solution (300 ml), dried over MgSO$_4$, and concentrated in vacuo. The crude material is purified by chromatography (silica gel; 1:9 EtOAc/hexanes 1:4 EtOAc/hexanes as solvent) affording the desired intermediate as a solid.

(k) 2-(3-biphenylylmethyl)-6-[2-(N-aminocarbonyl-N-hydroxyamino)ethoxy]-1-oxo-1,2,3,4tetrahydroiso m.p. 133°–135°;

(l) 2-(4'-fluoro-2-biphenylylmethyl)-6-[2-(N-aminocarbonyl-N-hydroxyamino)ethoxy]-1-oxo-1,2,3,4-tetrahydroisoquinoline, m.p. 123°–124°;

(m) 2-(4-biphenylymethyl)-6-[2-(N-aminocarbonyl-N-hydroxyamino)ethoxy]-3,4-dihydro-2H-1,2-benzothiazine-1,1-dioxide, m.p. 166°–167°;

(n) 2-(2-biphenylylmethyl)-6-[2-(N-aminocarbonyl-N-hydroxyamino)ethoxy]-3,4-dihydro-2H-1,2-benzothiazine-1,1-dioxide, m.p. 160°–161°; and (o) 2-(4'-fluoro-4-biphenylymethyl)-6-[2 -(N-aminocarbonyl-N-hydroxyamino)ethoxy]-3,4-dihydro-2H-1,2-benzothiazine-1,1-dioxide, m.p. 165°–166°.

EXAMPLE 14 a) Preparation of 10,000 tablets each containing 25 mg of the active ingredient, having the formula as follows:

| | |
|---|---|
| 2-[3-(4-fluorophenyl)-propyl]-6-[2-(N-aminocarbonyl- | 250.00 g |

-continued

| | |
|---|---|
| N-hydroxyamino)ethoxy]-1-oxo-1,2,3,4-tetrahydroisoquinoline | |
| Lactose | 2485.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10–100 mg of one of the other compounds disclosed and exemplified herein.

b) Preparation of 1,000 capsules each containing 50 mg of the active ingredient, having the formula as follows:

| | |
|---|---|
| 2-[3-(4-fluorophenyl)-propyl]-6-[2-(N-aminocarbonyl-N-hydroxyamino)ethoxy]-1-oxo-1,2,3,4-tetrahydroisoquinoline | 50.00 g |
| Lactose | 167.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

What is claimed is:

1. A compound of the formula

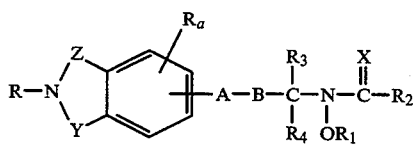

(I)

wherein

R represents hydrogen, lower alkyl, aryl, biaryl, $C_3$–$C_7$-cycloalkyl, aryl-lower alkyl, aryl-lower alkenyl, aryl-lower alkynyl, aryloxy-lower alkyl, arylthio-lower alkyl; $C_3$–$C_7$-cycloalkyl-lower alkyl, biaryl-lower alkyl, aryl-$C_3$–$C_7$-cycloalkyl, aryl-$C_3$–$C_7$-cycloalkyl-lower alkyl or aryloxy-aryl-lower alkyl; and aryl represents carbocyclic or heterocyclic aryl;

Z represents $C_1$-alkylene unsubstituted or substituted by lower alkyl;

Y represents $SO_2$ or CO;

A represents O, S, or a direct bond;

B represents lower alkylene; or B represents lower alkenylene provided that A represents a direct bond;

X represents oxygen or sulfur;

$R_1$ represents hydrogen, acyl, lower alkoxycarbonyl, aminocarbonyl, mono-or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$–$C_7$-cycloalkylaminocarbonyl or $C_3$–$C_7$-cycloalkyl-lower alkylaminocarbonyl;

$R_2$ represents lower alkyl, lower alkoxycarbonyl-lower alkyl, $C_3$–$C_7$-cycloalkyl, carbocyclic or heterocyclic aryl, carbocyclic or heterocyclic aryl-lower alkyl, $C_3$–$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$–$C_7$-cycloalkylamino, $C_3$–$C_7$-cycloalkyl-lower alkylamino or lower alkoxycarbonyl-lower alkylamino;

$R_3$ and $R_4$ independently represent hydrogen or lower alkyl;

$R_a$ represents hydrogen, lower alkyl, halo, trifluoromethyl or lower alkoxy; or a pharmaceutically acceptable salt thereof.

2. A compound according to claim 1 wherein Y represents CO.

3. A compound according to claim 1 wherein Y represents $SO_2$.

4. A compound according to claim 2 of the formula

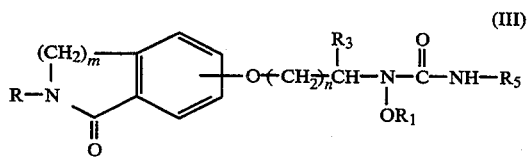

(III)

wherein R represents lower alkyl, biaryl-lower alkyl, carbocyclic or heterocyclic aryl-$C_1$–$C_4$-alkyl, carbocyclic or heterocyclic aryloxy-$C_1$–$C_4$-alkyl, carbocyclic aryloxyaryl-$C_1$–$C_4$-alkyl, carbocyclic aryl-$C_3$ or $C_4$-alkenyl, or cyclohexyl-$C_1$–$C_4$-alkyl; m represents 1; n represents 1, 2 or 3; $R_1$ represents hydrogen or acyl; $R_3$ represents hydrogen or lower alkyl; $R_5$ represents hydrogen, lower alkyl or monocyclic carbocyclic aryl; or a pharmaceutically acceptable salt thereof.

5. A pharmaceutical composition suitable for inhibiting 5-lipoxygenase activity in mammals comprising an effective 5-lipoxygenase inhibiting amount of a compound of claim 1 in combination with one or more pharmaceutically acceptable carriers.

6. A method of inhibiting 5-lipoxygenase activity and of treating disorders in mammals which are responsive to such inhibition which comprises administering to a mammal in need thereof an effective 5-lipoxygenase inhibiting amount of a compound of claim 1 or of a said compound in combination with one or more pharmaceutically acceptable carriers.

7. A method according to claim 6 of treating arthritic, pulmonary, inflammatory or allergic disorders.

* * * * *